United States Patent
Pan et al.

(10) Patent No.: US 9,750,670 B2
(45) Date of Patent: *Sep. 5, 2017

(54) ZINC AMINO ACID COMPLEX WITH CYSTEINE

(71) Applicant: Colgate-Palmolive Company, Piscataway, NJ (US)

(72) Inventors: Long Pan, Cherry Hill, NJ (US); Shaotang Yuan, East Brunswick, NJ (US); Shiri Nawrocki, Tenafly, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/650,898

(22) PCT Filed: Nov. 7, 2013

(86) PCT No.: PCT/US2013/068854
§ 371 (c)(1),
(2) Date: Jun. 10, 2015

(87) PCT Pub. No.: WO2014/099165
PCT Pub. Date: Jun. 26, 2014

(65) Prior Publication Data
US 2015/0313822 A1 Nov. 5, 2015

Related U.S. Application Data

(63) Continuation-in-part of application No. PCT/US2013/046268, filed on Jun. 18, 2013, and a continuation-in-part of application No. PCT/US2012/070489, filed on Dec. 19, 2012, and a continuation-in-part of application No. PCT/US2012/070492, filed on Dec. 19, 2012, and a continuation-in-part of application No. PCT/US2012/070498, filed on Dec. 19, 2012, and a continuation-in-part of application No. PCT/US2012/070506, filed on Dec. 19, 2012, and a continuation-in-part of application No. PCT/US2012/070513, filed on Dec. 19, 2012, and a continuation-in-part of application No. PCT/US2012/070505, filed on Dec. 19, 2012, and a continuation-in-part of application No. PCT/US2012/070501, filed on Dec. 19, 2012, and a continuation-in-part of application No. PCT/US2012/070521, filed on Dec. 19, 2012, and a continuation-in-part of application No. PCT/US2012/070534, filed on Dec. 19, 2012, and a continuation-in-part of application No. PCT/US2013/050845, filed on Jul. 17, 2013, and a continuation-in-part of application No. PCT/US2012/070537, filed on Dec. 19, 2012, and a continuation-in-part of application No. PCT/US2012/070525, filed on Dec. 19, 2012.

(51) Int. Cl.
*A61K 8/44* (2006.01)
*A61K 8/27* (2006.01)
*A61Q 15/00* (2006.01)
*A61Q 19/10* (2006.01)
*A61Q 19/00* (2006.01)
*A61Q 11/00* (2006.01)
*A61Q 17/00* (2006.01)

(52) U.S. Cl.
CPC .................. *A61K 8/27* (2013.01); *A61K 8/44* (2013.01); *A61K 8/442* (2013.01); *A61K 8/447* (2013.01); *A61Q 11/00* (2013.01); *A61Q 15/00* (2013.01); *A61Q 17/005* (2013.01); *A61Q 19/00* (2013.01); *A61K 2800/58* (2013.01); *A61K 2800/5922* (2013.01); *A61Q 19/10* (2013.01)

(58) Field of Classification Search
None
See application file for complete search history.

(56) References Cited

U.S. PATENT DOCUMENTS

| | | |
|---|---|---|
| 2,503,280 A | 4/1950 | Lockwood |
| 2,507,088 A | 5/1950 | Bradley |
| 2,527,686 A | 10/1950 | Sandberg |
| 2,893,918 A | 7/1959 | Abramson |
| 3,260,744 A | 7/1966 | Kenkichi |
| 3,320,174 A | 5/1967 | Rubinfeld |
| 3,372,188 A | 3/1968 | Terence |
| 3,535,421 A | 10/1970 | Briner |
| 3,538,230 A | 11/1970 | Morton |
| 3,678,154 A | 7/1972 | Briner |
| 3,741,911 A | 6/1973 | Shane |
| 3,862,307 A | 1/1975 | Giulio |
| 3,937,807 A | 2/1976 | Haefele |
| 3,941,818 A | 3/1976 | Abdel-Monem |
| 3,959,458 A | 5/1976 | Agricola et al. |

(Continued)

FOREIGN PATENT DOCUMENTS

| | | |
|---|---|---|
| CN | 1502330 A * | 6/2004 |
| CN | 101606639 | 12/2009 |
| CN | 102811698 | 12/2012 |
| CN | 103156073 | 6/2013 |
| CN | 103535536 | 1/2014 |
| DE | 735096 | 5/1943 |
| EP | 0083486 | 12/1982 |
| EP | 0108937 | 5/1984 |
| EP | 0508524 | 10/1992 |
| EP | 0514553 | 11/1992 |

(Continued)

OTHER PUBLICATIONS

Machine Translation of CN 1502330 A.*

(Continued)

*Primary Examiner* — Frederick Krass
*Assistant Examiner* — Michael P Cohen

(57) ABSTRACT

Provided are compositions, e.g., oral and personal care products, comprising (i) a tetrabasic zinc-amino acid or trialkyl glycine-halide complex, and (ii) cysteine in free or in orally or cosmetically acceptable salt form, together with methods of making and using the same.

18 Claims, No Drawings

(56) References Cited

U.S. PATENT DOCUMENTS

| | | |
|---|---|---|
| 4,051,234 A | 9/1977 | Gieske et al. |
| 4,316,824 A | 2/1982 | Pancheri |
| 4,339,432 A | 7/1982 | Ritchey et al. |
| 4,340,583 A | 7/1982 | Wason |
| 4,487,757 A | 12/1984 | Kiozpeoplou |
| 4,565,693 A | 1/1986 | Marschner |
| 4,599,152 A | 7/1986 | Ashmead |
| 4,684,528 A | 8/1987 | Godfrey |
| 4,687,663 A | 8/1987 | Schaeffer |
| 4,842,847 A | 6/1989 | Amjad |
| 4,866,161 A | 9/1989 | Sikes et al. |
| 4,885,155 A | 12/1989 | Parran, Jr. et al. |
| 5,004,597 A | 4/1991 | Majeti et al. |
| 5,061,815 A | 10/1991 | Leu |
| 5,156,845 A | 10/1992 | Grodberg |
| 5,188,821 A | 2/1993 | Gaffar et al. |
| 5,192,531 A | 3/1993 | Gaffar et al. |
| 5,504,055 A | 4/1996 | Hsu |
| 5,643,559 A | 7/1997 | Eigen et al. |
| 5,698,724 A | 12/1997 | Anderson et al. |
| 5,707,679 A | 1/1998 | Nelson |
| 5,714,447 A | 2/1998 | Jones et al. |
| 5,911,978 A | 6/1999 | Carr et al. |
| 5,993,784 A | 11/1999 | Hill |
| 6,121,315 A | 9/2000 | Nair et al. |
| 6,156,293 A | 12/2000 | Jutila et al. |
| 6,607,711 B2 | 8/2003 | Pedersen |
| 6,685,920 B2 | 2/2004 | Baig et al. |
| 6,969,510 B2 | 11/2005 | Holerca et al. |
| 8,067,627 B2 | 11/2011 | Newsome et al. |
| 8,247,398 B2 | 8/2012 | Goel |
| 2003/0003059 A1* | 1/2003 | Dana .................. A61K 8/986 424/49 |
| 2003/0012744 A1* | 1/2003 | Pedersen .............. A61K 8/27 424/49 |
| 2004/0033916 A1 | 2/2004 | Kuzmin et al. |
| 2004/0042978 A1 | 3/2004 | Embro |
| 2004/0122088 A1 | 6/2004 | Newsome et al. |
| 2004/0198998 A1 | 10/2004 | Holerca et al. |
| 2006/0024252 A1 | 2/2006 | Esposito et al. |
| 2007/0071698 A1 | 3/2007 | Doss |
| 2009/0220444 A1 | 9/2009 | Teckenbrock et al. |
| 2010/0021573 A1 | 1/2010 | Gonzalez et al. |
| 2010/0266480 A1 | 10/2010 | Huang |
| 2010/0330163 A1 | 12/2010 | Soparkar |
| 2011/0076309 A1 | 3/2011 | Misner et al. |
| 2011/0229536 A1 | 9/2011 | Kvitnitsky et al. |
| 2013/0017240 A1 | 1/2013 | Porter et al. |
| 2014/0170086 A1 | 6/2014 | Pan et al. |

FOREIGN PATENT DOCUMENTS

| | | | |
|---|---|---|---|
| EP | 0842664 | 5/1998 | |
| EP | 1021158 | 7/2000 | |
| EP | 1064946 | 1/2001 | |
| EP | 1203575 | 5/2002 | |
| EP | 1319394 | 6/2003 | |
| EP | 1935395 | 6/2008 | |
| EP | 1529775 | 5/2011 | |
| FR | 2241301 | 3/1975 | |
| GB | 2052978 | 2/1981 | |
| GB | 2109685 | 6/1983 | |
| GB | 2243775 | 11/1991 | |
| JP | S57-158724 | 9/1982 | |
| JP | 2004175790 | 6/2004 | |
| JP | 2009084201 | 4/2009 | |
| JP | 2010132639 | 6/2010 | |
| WO | WO86/00004 | 1/1986 | |
| WO | WO9917735 | 4/1999 | |
| WO | WO0169087 | 9/2001 | |
| WO | WO2004054531 | 7/2004 | |
| WO | WO2004/064536 | 8/2004 | |
| WO | WO2007063507 | 6/2007 | |
| WO | WO 2011005577 A1 * | 1/2011 | ............. A23L 1/304 |
| WO | WO2011053291 | 5/2011 | |
| WO | WO2011/088199 | 7/2011 | |
| WO | WO2011/123123 | 10/2011 | |
| WO | WO2014/098813 | 6/2014 | |
| WO | WO2014/098814 | 6/2014 | |
| WO | WO2014/098818 | 6/2014 | |
| WO | WO2014/098819 | 6/2014 | |
| WO | WO2014/098821 | 6/2014 | |
| WO | WO2014/098822 | 6/2014 | |
| WO | WO2014/098824 | 6/2014 | |
| WO | WO2014/099164 | 6/2014 | |
| WO | WO2014/099165 | 6/2014 | |
| WO | WO2014/099166 | 6/2014 | |
| WO | WO2014/099167 | 6/2014 | |
| WO | WO2014098825 | 6/2014 | |
| WO | WO2014098826 | 6/2014 | |
| WO | WO2014098828 | 6/2014 | |
| WO | WO2014098829 | 6/2014 | |
| WO | WO2014099039 | 6/2014 | |
| WO | WO2014099226 | 6/2014 | |
| WO | WO2014204439 | 12/2014 | |

OTHER PUBLICATIONS

Definition of "complex". Downloaded from http://www.chemicool.com/definition/complex.html, on Aug. 25, 2016. 3 printed pages.*

Anonymous, "Zinc Lauryl Ether Sulphate, A New Approach to Skincare,", Apr. 2004, Retrieved from Internet, http://www.erwebhosting.it/zsi/repository/Zinc%20Lauryl%20Ether%20Sulphate,%20A%20new%20approach%20to%20skin%20care.pdf, Retrieved Sep. 26, 2013.

Deschaume et al., "Interactions of aluminum hydrolytic species with biomolecules," New Journal of Chemistry, 2008, 32:1346-1353.

European Food Safety Authority, "Scientific Opinion on the safety and efficacy of tetra-basic zinc chloride for all animal species," EFSA Journal, 2012, 10(5):2672.

Hartwell et al., "Preparation and characterization of tyrosine and lysine metal chelate polyesters and polyamides", J. of the American Chem. Society, Mar. 1970, 92(5):1284-1289.

International Search Report and Written Opinion for International Application No. PCT/US2012/070489 mailed on Oct. 22, 2013.
International Search Report and Written Opinion for International Application No. PCT/US2012/070492 mailed on Oct. 22, 2013.
International Search Report and Written Opinion for International Application No. PCT/US2012/070498 mailed on Sep. 4, 2013.
International Search Report and Written Opinion for International Application No. PCT/US2012/070501 mailed on Oct. 21, 2013.
International Search Report and Written Opinion for International Application No. PCT/US2012/070505 mailed on Nov. 20, 2013.
International Search Report and Written Opinion for International Application No. PCT/US2012/070506 mailed on Oct. 14, 2013.
International Search Report and Written Opinion for International Application No. PCT/US2012/070513 mailed on Oct. 14, 2013.
International Search Report and Written Opinion for International Application No. PCT/US2012/070521 mailed on Sep. 30, 2013.
International Search Report and Written Opinion for International Application No. PCT/US2012/070525 mailed on Sep. 27, 2013.
International Search Report and Written Opinion for International Application No. PCT/US2012/070528 mailed on Sep. 30, 2013.
International Search Report and Written Opinion for International Application No. PCT/US2012/070534 mailed on Sep. 26, 2013.
International Search Report and Written Opinion for International Application No. PCT/US2012/070537 mailed on Oct. 11, 2013.
International Search Report and Written Opinion for International Application No. PCT/US2013/046268 mailed on Apr. 22, 2014.
International Search Report and Written Opinion for International Application No. PCT/US2013/050845 mailed on Aug. 13, 2014.
International Search Report and Written Opinion for International Application No. PCT/US2013/068852 mailed on Nov. 10, 2014.
International Search Report and Written Opinion for International Application No. PCT/US2013/068854 mailed on Oct. 20, 2014.

(56) References Cited

OTHER PUBLICATIONS

International Search Report and Written Opinion for International Application No. PCT/US2013/068859 mailed on Aug. 4, 2014.
International Search Report and Written Opinion for International Application No. PCT/US2013/068860 mailed on Oct. 22, 2014.
International Search Report and Written Opinion for International Application No. PCT/US2013/070932 mailed on Jul. 24, 2014.
International Search Report and Written Opinion for International Application No. PCT/US2014/042947 mailed on Aug. 22, 2014.
International Search Report and Written Opinion for International Application No. PCT/US2014/042948 mailed on Aug. 26, 2014.
International Search Report and Written Opinion for International Application No. PCT/US2014/043051 mailed on Feb. 18, 2015.
Kondrot, "The Importance of Zinc," http://www.healingtheeye.com/Articles/zinc.html, Feb. 21, 2012.
Liang et al., "In vitro scratch assay: a convenient and inexpensive method for analysis of cell migration in vitro," Nature Protocols, 2007, 2(2):329-333.
Liu et al., "The research on zinc coordination No. 5 odd structure in zinc complex with L-lysine," J. Molecular Science, 2000, 16(2):114-117, abstract only in English.
Lu et al., "Albumin as a zinc carrier: properties of its high-affinity zinc-binding site". Biochem. Soc. Trans., 2008, 36:1317-1321.
Lynch, "Zinc in the mouth, its interactions with dental enamel and possible effects on caries: a review of the literature," Int. Dent. J., Aug. 2011, suppl 3:46-54.
Mavromichalis et al., "Growth-promoting efficacy of pharmacological doses of tetrabasic zinc chloride in diets for nursery pigs," Canadian Journal of Animal Science, pp. 387-391, Jan. 2001.
McAuliffe et al., "Metal complexes of sulphur-containing amino acids," Inorganica Chimica Acta Reviews, Dec. 1972, 6:103-121.
Moore et al., "Antibacterial activity of gutta-percha cones attributed to the zinc oxide component," Oral Surgery, 1982, 53:508-517.
Mosmann, "Rapid colorimetric assay for cellular growth and survival: Application to proliferation and cytotoxicity assays," J. Immunol. Methods, 1983, 65:55-63.
Pashley et al. Dentin permeability effects of desensitizing dentifries in vitro. J Periodontol. 1984;55(9):522-525.

Prasad, "Zinc:role in immunity, oxidative stress and chronic inflammation," Current Opinion in Clinical Nutrition and Metabolic Care, 2009, 12:646-652.
Rigano, L., Zinc Lauryl Ether Sulphate—A New Approach to Skin Care, SOFW Journal, Apr. 2004, 128:26-33.
Schmetzer et al., "Wulfingite, $\epsilon$-Zn(OH)2, and simonkolleite, Zn5(OH)8Cl2•H2O, two new minerals from Richelsdorf, Hesse, F.R.G.," N. Jb. Miner. Mh., Apr. 1985, pp. 145-154.
Seil et al., "Antibacterial effect of zinc oxide nanoparticles combined with ultrasound," Nanotechology,2012, 23:495101.
Soderling et al., "Betaine-containing toothpaste relieves subjective symptoms of dry mouth," Acta Odontol. Scand., Apr. 1998, 56(2):65-9.
Stewart et al., "Interdomain zinc site on human albumin," PNAS, 2003, 100(7):3701-3706.
Tian, et al., "Using DGGE profiling to develop a novel culture medium suitable for oral microbial communities," Molecular Oral Microbiology, 2010, 25(5):357-367.
Twetman et al., 2003, "Caries-preventative effect of fluoride toothpaste a systematic review," Acta Odontol Scand., Dec. 2003, 61(6):347-55.
Wachi et al., "Antibacterial compsn. Zinc oxide—solubilized by amino acid, amino acid hydrochloride and/or amino acid alkali metal salt," Sep. 1982, vol. 1982(45).
Wallhausser et al., "Antimicrobial Preservatives in Europe: Experience with preservatives used in pharmaceuticals and cosmetics," Develop. Biol. Standard, 1974, 24:9-28.
Yao et al., "An investigation of zirconium(IV)-glycine(CP-2) hybrid complex in bovine serum albumin protein matrix under varying conditions," J. of Materials Chemistry, 2011, 21:19005-19012.
Yousef et al., "In vitro antibacterial activity and minimum inhibitory concentration of zinc oxide and nano-particle zinc oxide against pathogenic strains," J. of Health Sciences, 2012, 2(4):38-42.
Zhu et al., "Synthesis and Crystal Structure of [Zn+{H2N(CH2)4CH(NH2)COONa}2SO4-] •H20," Chinese Science Bulletin, Sep. 1990, 35(18):1521-1525.
Corresponding Chinese Search Report dated Aug. 17, 2016.
Complex, Tolkovyi slovar Ozhegova [Ozhegov's explanatory dictionary], S.I. Ozhegov, N. Yu. Shvedova, 1949-1992, found on Jul. 20, 2016], (http://dic.academic.ru/dic.nsf/ogegova/87110-KOMPLEKS>).

* cited by examiner

ZINC AMINO ACID COMPLEX WITH CYSTEINE

CROSS REFERENCE TO RELATED APPLICATIONS

This application is a continuation in part of PCT/US2013/46268, filed on 18 Jun. 2013; PCT/US2012/70489, filed on 19 Dec. 2012; PCT/US2012/70492, filed on 19 Dec. 2012; PCT/US2012/70498, filed on 19 Dec. 2012; PCT/US2012/70506, filed on 19 Dec. 2012; PCT/US2012/70513, filed on 19 Dec. 2012; PCT/US2012/70505, filed on 19 Dec. 2012; PCT/US2012/70501, filed on 19 Dec. 2012; PCT/US2012/70521, filed on 19 Dec. 2012; PCT/US2012/70534, filed on 19 Dec. 2012; PCT/US2013/70537, filed on 19 Dec. 2012; PCT/US2012/70525, filed on 19 Dec. 2012; and PCT/US2013/50845, filed on 17 Jul. 2013, all of which are incorporated herein by reference.

BACKGROUND

Conventional antiperspirants comprising salts of aluminum or aluminum/zirconium are known. These salts function as antiperspirants by forming polymeric complexes which can plug pores, thereby blocking sweat release. There is a need for additional antiperspirant active agents that provide molecular weight complexes of a size capable of plugging pores to block sweat, that provide deodorant/antibacterial efficacy, and that are less irritating to the skin than the acidic salts in conventional antiperspirants. There is also a need for alternative antibacterial and skin protective agents for use in liquid hand soaps and body washes. Finally, there is a need for agents in oral care products which can whiten and strengthen teeth, retard erosion, and inhibit bacteria and plaque.

BRIEF SUMMARY

Provided is a composition comprising a complex of tetrabasic zinc halide ("TBZH"), e.g., tetrabasic zinc chloride ("TBZC"), and an amino acid or trialkylglycine (TAG) (respectively, "TBZH-AA", "TBZC-AA", "TBZH-TAG" and "TBZC-TAG) in combination with cysteine, which complex is stable and soluble in concentrated aqueous solution, but which provides a relatively acid-stable precipitate comprising a complex of zinc and cysteine upon dilution. The unusual and unexpected properties of this material allow delivery of a stable zinc complex to the skin or teeth, making it useful in personal care products, e.g., antiperspirant products and liquid hand and body soaps, as well as in oral care products, e.g. mouthwash or dentifrice.

Tetrabasic zinc chloride (TBZC) or zinc chloride hydroxide monohydrate is a zinc hydroxy compound with the formula $Zn_5(OH)_8Cl_2.H_2O$, also referred to as basic zinc chloride, zinc hydroxychloride, or zinc oxychloride. It is a colorless crystalline solid insoluble in water. While TBZC is substantially insoluble in water, the material is found to be soluble in water in the presence of an amino acid and provides a source of zinc ions without the usage of additional anions (i.e. HCl). While TBZC is preferred in the compositions and methods, other tetrabasic zinc halides may be used, e.g., tetrabasic zinc fluoride or tetrabasic zinc bromide.

The TBZH-AA or TBZH-TAG complex contains a halide such as chloride. In one embodiment, the TBZH-AA or TBZH-TAG is formed by reacting TBZH with the free base of the amino acid, in such case the halide (e.g., chloride) contribution to the complex will be primarily from TBZH. In another embodiment, the TBZH-AA is formed by reacting TBZH and a hydrohalide salt (e.g., hydrochloride salt) of a basic amino acid to obtain a complex containing TBZH the basic amino acid and halide, in such case the halide contribution to the complex will be from the TBZH and the hydrohalide salt of the amino acid. In other embodiments, a combination of the free base and hydrohalide salt of the amino acid is used as a starting material, and in other embodiments, additional halides can be provided via addition of different halide-containing compounds such as hydrochloric acid, hydrobromide acid, and the like. The types and amounts of halide source can be manipulated to achieve a desired pH.

In one embodiment, the TBZH-AA is a TBZC-lysine complex, e.g., formed from a mixture of TBZC and lysine and/or lysine hydrochloride. This particular zinc-lysine-chloride complex is sometimes referred to herein as "TBZC-Lys".

The tetrabasic zinc-amino acid or TAG-halide complexes, e.g. TBZC-Lys, have key features (e.g., conductivity, hydrolysis reaction and protein flocculation) which make it competitive with commercial antiperspirant salts. Like conventional aluminum or aluminum-zirconium antiperspirant salts, the TBZH-AA or TBZH-TAG forms precipitates under sweat conditions that can plug the pores and block sweat release. The mechanism is unusual. As the amount of water increases, rather than going into or remaining in solution as the solution becomes more dilute, as would typically be the case for an ionic complex, the TBZH-AA or TBZH-TAG hydrolyzes, to provide a relatively insoluble zinc-containing precipitate, e.g. zinc oxide, thereby permitting further plugging of the pores and/or controlled deposition of zinc compounds on the skin. The zinc is moreover antibacterial, and so in addition to providing a precipitate which blocks sweat release from the pores, it provides a deodorant benefit by reducing odor-causing bacteria The precipitate formed from the complexes typically contains zinc oxide, as well as other compounds and/or complexes. Zinc oxide, one constituent in the precipitate, is soluble at acidic pH, however, and as sweat has a pH of 5-6, the sweat can reduce the levels of precipitation as compared to precipitation levels at neutral or higher pH. Moreover, the sweat can gradually dissolve the depositions, reducing the duration of action of the formulation. Also, the rate of precipitation may be too slow or too rapid. These problems can be ameliorated by co-formulating the product with cysteine. The cysteine and the zinc complex together form a precipitate upon use and dilution with sweat, which precipitate can be resistant to acid. The formulation comprising TBZH-AA or TBZH-TAG together with cysteine thus has enhanced efficacy as an antiperspirant. Moreover, the cysteine helps stabilize the TBZH-AA or TBZH-TAG in the formulation prior to administration.

Although we have found that use of cysteine with the TBZH-AA or TBZH-TAG complexes form precipitates that are more resistant to sweat, we have also discovered that use of cysteine delays, or under some conditions, even inhibits formation of the precipitate. The amount of cysteine and the pH have an effect on the degree and rate of precipitate formation.

The pH of the composition will vary based on factors such as the amount of water, cysteine concentration and the like. The pH of the composition is generally 7 to 11, in another embodiment 7 to 10, in another embodiment 8 to 10, in another embodiment 8 and 9.

The compositions can contain from 0.01 to 1% cysteine by weight. Surprisingly, it has been found that the amount of cysteine in the formulation can influence precipitation and acid resistance. For example, formulations containing cysteine at levels of 0.09% cysteine or less typically exhibit precipitation upon dilution but poor acid resistance. Formulations containing 0.1% to less than 0.15% cysteine typically exhibit instant precipitation upon dilution and good acid resistance that can withstand a pH alteration of up to 5 pH units. Formulations containing 0.15% or greater cysteine typically exhibit delayed precipitation upon dilution and good acid resistance. "Acid resistance" in this context refers to the property of maintaining a precipitate, or preventing the solubilization of a precipitate, in an aqueous solution at a pH similar to human sweat, i.e., a pH-t of 5.5. "Precipitation" in this context refers to formation of an insoluble precipitate upon dilution that is visible to the naked eye, e.g., visible particles in a solution or visible cloudiness or turbidity of a previous transparent solution. "Dilution" for the purposes of this paragraph refers to a four (4) fold or more dilution, which typically contains 95% of water or higher. "Instant precipitation" refers to the precipitation is observed in less than 1 second after dilution of the TBZH-AA or TBZH-TAG complex/cysteine combination. "Delayed precipitation" refers to that precipitation is observed 1 second to 180 seconds, in another embodiment 1 to 60 seconds, and in another embodiment 1 to 10 seconds, after dilution of the TBZH-AA or TBZH-TAG complex/cysteine combination.

The compositions in undiluted form generally contain 10 to 90%, in another embodiment 20 to 90% and in another embodiment 50 to 90% water, but can contain much less water in some embodiments. The amount of water in the compositions will vary depending upon the final product form in order to achieve the desired concentration. For example, dentifrices typically contain 10 to 25% total water, mouthwashes typically contain 50 to 90% total water, personal care products such as antiperspirants typically contain 10 to 20% total water. The precipitation time and pH values of the mixtures are affected by many factors, including water concentration. More water generally leads to more rapid precipitation and higher pH values.

In another embodiment, the TBZH-AA or TBZH-TAG/cysteine combination is also useful in liquid hand soaps and body washes.

In yet another embodiment, the TBZH-AA or TBZH-TAG/cysteine combination is useful in oral care products, for example dentifrice or mouthwash (mouth rinse). A formulation comprising the TBZH-AA or TBZH-TAG/cysteine combination provides an effective concentration of zinc ions to the enamel, thereby protecting against erosion, reducing bacterial colonization and biofilm development, and providing enhanced shine to the teeth. Moreover, upon use, the formulation is diluted and provides a stabilized precipitate that plugs the dentinal tubules, thereby reducing the sensitivity of the teeth. While providing efficient delivery of zinc in comparison to formulations with insoluble zinc salts, the formulations comprising the TBZH-AA or TBZH-TAG/cysteine combination do not exhibit the poor taste and mouthfeel, poor fluoride delivery, and poor foaming and cleaning associated with conventional zinc-based oral care products using soluble zinc salts.

Compositions exhibiting delayed precipitation can be particularly advantageous to maximize the amount of precipitation at the desired site during use, e.g., at dentinal tubules or sweat glands.

Provided is a composition comprising (i) a tetrabasic zinc-amino acid or TAG-halide complex (preferably TBZC-AA), e.g., TBZC-Lys, and (ii) cysteine in free or in orally or cosmetically acceptable salt form. The compositions may be oral care products, e.g., dentifrice or mouth rinse (or mouthwash), or personal care products, such as antiperspirants, liquid hand soap or body wash, and skin lotions, creams and conditioners. Further provided are methods of using such compositions, e.g., methods of reducing sweat comprising applying the composition to skin, methods of killing bacteria comprising contacting the bacteria with the composition, and methods of treating or reducing dental hypersensitivity, erosion, and plaque, comprising applying the composition to the teeth, as well as methods of making such compositions.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In one embodiment, a single-component delivery system in the form of a mouthrinse is contemplated, where the system comprises a concentrated solution of the TBZH-AA or TBZH-TAG/cys complex and the diluent is supplied by the administrator/user either in the form of water naturally involved in a typical oral care treatment and/or saliva generated by the user.

Provided is, in a first embodiment, a composition (Composition 1) comprising (i) a tetrabasic zinc-amino acid or TAG-halide complex and (ii) cysteine in free or in orally or cosmetically acceptable salt form, e.g., 1.1. Composition 1 wherein the zinc-amino acid or TAG-halide complex is formed from precursors, wherein the precursors are TBZC, an amino acid source, and a chloride source, wherein the chloride source can be part of the TBZC, the amino acid source, or hydrochloric acid.
1.2. Composition 1.1 wherein the amino acid source is at least one of a basic amino acid, lysine, arginine, and glycine.
1.3. Any of the foregoing compositions, wherein the trialkyl glycine is a $C_1$-$C_4$ alkyl glycine or trimethyl glycine.
1.4. Any of the foregoing Compositions wherein the TBZH-AA complex is made by combining TBZC with an amino acid hydrochloride.
1.5. Any of the foregoing Compositions wherein the TBZH-AA complex is TBZC-Lys.
1.6. Any of the foregoing Compositions which upon dilution with water, provides a precipitate comprising of an insoluble zinc-containing precipitate in complex with cysteine.

1.7. Any of the foregoing Compositions wherein the total amount of zinc present in the composition is 0.2 to 8% by weight of the composition.

1.8. Any of the foregoing compositions wherein the ratio of zinc to cysteine is 10:1 to 100:1 by weight.

1.9. Any of the foregoing compositions wherein the pH is 8.4 to 8.8.

1.10. Any of the foregoing compositions, wherein the cysteine is a cysteine hydrohalide, optionally cysteine hydrochloride.

1.11. Any of the foregoing compositions further comprising an orally or cosmetically acceptable carrier.

1.12. Any of the foregoing compositions further comprising an orally or cosmetically acceptable carrier, and which is an oral care product selected from dentifrice or mouthwash, or a personal care product, selected from antiperspirants, deodorants, liquid hand soap, body wash, dermal lotions, dermal creams, and dermal conditioners.

1.13. Any of the foregoing compositions further comprising an orally or cosmetically acceptable carrier that comprises less than 10% water, e.g., less than 5% water, e.g., is substantially anhydrous.

1.14. Any of the foregoing compositions wherein the composition comprises not more than 85% water.

1.15. Any of the foregoing compositions comprising 0.09 to 0.15% cysteine.

1.16. Any of the foregoing compositions which instantly, e.g. 1 second or less after dilution, forms a precipitate upon a four-fold or higher dilution with water or an aqueous solution such as saliva or sweat.

1.17. Any of the foregoing compositions which forms a delayed precipitate, e.g., greater than 1 second, greater than 1 second to 180 seconds, 1 second to 60 seconds, or 1 second to 10 seconds, after a four-fold or higher dilution with water or an aqueous solution such as saliva or sweat.

1.18. Any of the foregoing compositions comprising an amount of cysteine effective to provide delayed precipitation, e.g., 0.09 to 0.15%.

1.19. Any of the foregoing compositions capable of forming a precipitate upon a four-fold or higher dilution with water or an aqueous solution such as saliva or sweat, wherein the precipitate has acid resistance at a pH of 5.5.

1.20. Any of the foregoing compositions comprising 0.2 to 8 weight % zinc.

Provided is a method of making composition 1, et seq. comprising (i) combining TBZH, an amino acid source, and a halide source (wherein the halide source can be part of TBZH, the amino acid source, or hydrohalide acid), in a fluid (e.g., aqueous) medium, optionally isolating the complex thus formed in solid form, combining the complex with cysteine, or (ii) combining a TBZH-AA complex and cysteine. The mixture can optionally be combined with a cosmetically acceptable carrier.

Provided is a composition (Composition 2) which is an antiperspirant or deodorant product comprising (i) a TBZH-AA or TBZH-TAG complex and (ii) cysteine in free or in cosmetically acceptable salt form, together with a cosmetically acceptable carrier, e.g. in accordance with any of the scopes of Composition 1, et seq., e.g.

2.1. Composition 2 which, upon use and, provides a precipitate to the skin comprising an insoluble zinc-containing complex.

2.2. Composition 2 or 2.1 wherein TBZH-AA complex is TBZC-Lys, optionally in hydrate form.

2.3. Composition 2, 2.1 or 2.2 wherein the cosmetically acceptable carrier comprises one or more ingredients selected from water-soluble alcohols (such as $C_{2-8}$ alcohols including ethanol); glycols (including propylene glycol, dipropylene glycol, tripropylene glycol and mixtures thereof); glycerides (including mono-, di- and triglycerides); medium to long chain organic acids, alcohols and esters; surfactants (including emulsifying and dispersing agents); additional amino acids; structurants (including thickeners and gelling agents, for example polymers, silicates and silicon dioxide); emollients; fragrances; and colorants (including dyes and pigments).

2.4. Composition 2, 2.1, 2.2 or 2.3 wherein the composition is in the form of an antiperspirant stick, an aerosol antiperspirant spray, or a liquid roll-on antiperspirant.

Also provided are methods of reducing perspiration comprising applying an antiperspirant effective amount of any of Composition 2, et seq. to the skin, methods of reducing body odor comprising applying a deodorant-effective amount of any of Composition 2, et seq. to the skin, and methods of killing bacteria comprising contacting the bacteria with contacting with any of Composition 2, et seq. For example, provided is (i) a method for controlling perspiration comprising applying to skin an antiperspirant effective amount of a formulation of any embodiment embraced or specifically described herein, e.g., any of Composition 2, et seq.; and (ii) a method for controlling odor from perspiration or bacteria on the skin, comprising applying to skin a deodorant effective amount of a formulation of any embodiment embraced or specifically described herein, e.g., any of Composition 2, et seq.

Provided is a method of making an antiperspirant or deodorant comprising (i) a TBZH-AA complex and (ii) cysteine in free or cosmetically acceptable salt form, e.g., any of Composition 2, et seq. comprising combining TBZC-Lys, cysteine and a cosmetically acceptable carrier.

Also provided is (i) the use of any of Composition 2, et seq. to kill bacteria, reduce perspiration, and/or reduce body odor; and (iii) any of Composition 2, et seq. for use in killing bacteria, reducing perspiration, and/or reducing body odor.

Also provided is the use of cysteine in the manufacture of an antiperspirant or deodorant formulation, e.g., a formulation according to any of Composition 2, et seq.

In making Composition 2, et seq. the TBZH-AA or TBZH-TAG and cysteine in free or cosmetically acceptable salt form can be incorporated into a suitable, cosmetically acceptable base, for example a stick, roll-on, spray or aerosol, for application to the underarm. Following application, in the presence of charged molecules such as proteins found on the skin, the salt will flocculate, forming plugs which block sweat release. Additional water from sweat can moreover dilute the formulation, causing the complex to decompose, resulting in a precipitate comprised of zinc oxide in complex with cysteine, which can reduce sweat and odor as described above.

As used herein, the term antiperspirant can refer generally to any product that can form a plug in a pore to reduce sweating, including those materials classified as antiperspirants by the Food and Drug Administration under 21 CFR part 350. It is understood that antiperspirants may also be deodorants, particularly in the case of the described compositions, as zinc has antibacterial properties and thus inhibits odor-causing bacteria on the skin.

Also provided is a composition (Composition 3) which is a personal care product selected from liquid hand soap, body wash, dermal lotions, dermal creams, and dermal conditioners comprising (i) a TBZH-AA or TBZH-TAG complex and (ii) cysteine in free or cosmetically acceptable salt form, together with a cosmetically acceptable carrier, e.g. in accordance with any of the scopes of Composition 1, et seq., e.g.

3.1. Composition 3 which, upon use with water, provides an insoluble zinc-containing precipitate to the skin.
3.2. Composition 3 or 3.1 comprising the TBZH-AA or TBZH-TAG complex in an amount of 1 to 10% by weight of the composition.
2.5. Any of the foregoing compositions wherein the TBZH-AA complex is TBZC-Lys, optionally in hydrate form.
3.3. Any of the foregoing compositions, wherein a total amount of zinc present in the composition is 0.1 to 8 weight %, optionally 0.1 to 2 or 0.1 to 1 weight %.
3.4. Any of the foregoing compositions, wherein the cysteine is a cysteine hydrohalide, optionally cysteine hydrochloride.
3.5. Any of the foregoing compositions wherein the cosmetically acceptable carrier comprises one or more ingredients selected from water-soluble alcohols (such as $C_{2-8}$ alcohols including ethanol); glycols (including propylene glycol, dipropylene glycol, tripropylene glycol and mixtures thereof); glycerides (including mono-, di- and triglycerides); medium to long chain organic acids, alcohols and esters; surfactants (including emulsifying and dispersing agents); additional amino acids; structurants (including thickeners and gelling agents, for example polymers, silicates and silicon dioxide); emollients; fragrances; and colorants (including dyes and pigments).
3.6. Any of the foregoing compositions, wherein the cosmetically acceptable carrier comprises one or more non-ionic surfactants, for example non-ionic surfactants selected from amine oxide surfactants (e.g., fatty acid amides of alkyl amines, for example lauramidopropyldimethylamine oxide, myristamidopropylamine oxide and mixtures thereof), alcohol amide surfactants (e.g., fatty acid amides of alcohol amines, e.g., cocamide MEA (cocomonoethanolamide)), polyethoxylated surfactants (e.g. polyethoxylated derivatives of esters of fatty acids and polyols (for example glycols, glycerols, saccharides or sugar alcohols), for example polysorbates or PEG-120 methyl glucose dioleate), and combinations thereof.
3.7. Any of the foregoing compositions wherein the cosmetically acceptable carrier comprises an anionic surfactant, e.g. selected from sodium lauryl sulfate and sodium ether lauryl sulfate.
3.8. Any of the foregoing compositions wherein the cosmetically acceptable carrier comprises water, an anionic surfactant, e.g., sodium laureth sulfate, a viscosity modifying agent, e.g., acrylates copolymer, and a zwitterionic surfactant, e.g., cocamidopropyl betaine.
3.9. Any of the foregoing compositions wherein the cosmetically acceptable carrier is substantially free of anionic surfactants.
3.10. Any of the foregoing compositions wherein the cosmetically acceptable carrier comprises water, quaternary ammonium agents (e.g. cetrimonium chloride), humectant (e.g. glycerin), and non-ionic surfactant (e.g., selected from amine oxide surfactants (e.g., lauramidopropyldimethylamine oxide myristamidopropylamine oxide and mixtures thereof), alcohol amide surfactants (e.g., cocamide MEA (cocomonoethanolamide)), polyethoxylate surfactants (e.g. PEG-120 methyl glucose dioleate), and combinations thereof).
3.11. Any of the foregoing compositions, wherein the cosmetically acceptable carrier comprises an antibacterially effective amount of a non-zinc antibacterial agent, e.g., an antibacterial agent selected from triclosan, triclocarban, chloroxylenol, herbal extracts and essential oils (e.g. rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid), bisguanide antiseptics (e.g., chlorhexidine, alexidine or octenidine), and quaternary ammonium compounds (e.g., cetylpyridinium chloride (CPC), benzalkonium chloride, tetradecylpyridinium chloride (TPC), N-tetradecyl-4-ethylpyridinium chloride (TDEPC)); and combinations thereof; for example an antibacterially effective amount of benzalkonium chloride.
3.12. Any of the foregoing compositions which has slightly alkaline pH.
3.13. Any of the foregoing compositions comprising ingredients as follows:

| Material | Weight % |
| --- | --- |
| Water | 80-95% |
| Quaternary ammonium antibacterial agents, e.g., selected from cetrimonium chloride (cetyl trimethyl ammonium chloride), $C_{12-18}$ alkydimethylbenzyl ammonium chloride (BKC), and combinations thereof | 0.1-4% |
| Humectants, e.g., glycerin | 1-3% |
| Non-ionic surfactant, e.g., selected from amine oxide surfactants (e.g., lauramidopropyldimethylamine oxide myristamidopropylamine oxide and mixtures thereof), alcohol amide surfactants (e.g., cocamide MEA (cocomonoethanolamide)), polyethoxylate surfactants (e.g. PEG-120 methyl glucose dioleate), and combinations thereof | 1-5% |
| Buffering agents and agents to adjust pH | 1-3% |
| Preservatives and/or chelators | 0.1-2% |
| Fragrance and coloring agents | 0.1-2% |
| TBZC-AA | 1-10%, e.g., 3-4% |
| Cysteine | 0.1-1%, e.g. 0.5% |

Also provided are methods of killing bacteria comprising contacting the bacteria with an antibacterially effective amount of a TBZH-AA/cys complex, e.g., with any of Composition 3, et seq., for example, methods of treating or reducing the incidence of topical skin infections, for example infections by *Staphylococcus aureus* and/or *Streptococcus pyogenes*, as well as to treat or reduce the incidence of acne, comprising washing the skin with an antibacterially effective amount of a TBCH-AA and cysteine, e.g., with any of Composition 3, et seq., and water.

Also provided is a method of making a personal care composition comprising (i) a TBZH-AA or TBZH-TAG complex and (ii) cysteine in free or cosmetically acceptable salt form, e.g., any of Composition 3, et seq. comprising combining (i) combining TBZH, an amino acid source, and a halide source (wherein the halide source can be part of the TBZH, the amino acid source, or hydrohalide acid such as hydrochloric acid), in a fluid (e.g., aqueous) medium, optionally isolating the complex thus formed in solid form, combining the complex with cysteine, or (ii) combining a TBZH-AA or TBZH-TAG complex and cysteine. The TBZH-AA or TBZH-TAG complex and cysteine are combined with a cosmetically acceptable carrier. Also provided is (i) the use of a TBZH-AA or TBZH-TAG complex and cysteine, e.g., any of Compositions 1, et seq., to kill bacteria, to protect the skin, e.g., from bacteria or to provide a visual signal when washing; (ii) the use of a TBZH-AA or TBZH-TAG and cysteine in the manufacture of a composition, any of Compositions 1, et seq., to kill bacteria, to protect the skin, or to provide a visual signal when washing; and (iii) TBZH and cysteine, e.g., any of Compositions 1, et seq., for use to kill bacteria, to protect the skin, or to provide a visual signal when washing.

For example, in one embodiment, the TBZH-AA or TBZH-TAG complex and the cysteine are incorporated into a conventional commercial liquid hand soap (LHS) formulation comprising surfactants and optionally benzalkonium chloride. The salt is found to be compatible with the formula and generates a transparent solution. Upon dilution, however, the combination instantly forms a white precipitate. Thus, TBZH-AA complex and the cysteine in a surfactant base can provide a visual/sensory trigger for the washing process. The precipitate, comprising ZnO stabilized by cysteine, is deposited on skin and thus enhances the antimicrobial effect of the LHS.

Also provided is a composition (Composition 4) which is an oral care product, e.g., a dentifrice or mouth rinse, comprising (i) a TBZH-AA or TBZH-TAG complex and (ii) cysteine in free or orally acceptable salt form, together with an orally acceptable carrier, e.g. in accordance with any of the scopes of Composition 1, et seq., e.g.

4.1. Composition 4 in the form of a dentifrice which upon application to the teeth in the presence of water, provides an insoluble zinc-containing complex to the teeth.
4.2. Composition 4 or 4.1 in the form of a dentifrice wherein the TBZH-AA complex is present in an effective amount, e.g., in an amount of 0.5-4% by weight of zinc, e.g., 1-3% by weight of zinc, and wherein the orally acceptable carrier is a dentifrice base.
4.3. Any of the foregoing compositions wherein the TBZH-AA complex is TBZC-Lys, optionally in hydrate form.
4.4. Any of the foregoing compositions 4-4.2 in the form of a dentifrice, wherein the orally acceptable carrier is a dentifrice base comprising an abrasive, e.g., an effective amount of a silica abrasive, e.g., 10-30%, e.g., 20%.
4.5. Any of the foregoing compositions wherein the TBZH-AA or TBZH-TAG complex is present in an effective amount, e.g., in an amount of 0.2 to 8% by weight of zinc.
4.6. Any of the foregoing compositions, wherein the cysteine is a cysteine hydrohalide, optionally cysteine hydrochloride.
4.7. Any of the foregoing compositions further comprising an effective amount of a fluoride ion source, e.g., providing 500 to 3000 ppm fluoride.
4.8. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.
4.9. Any of the foregoing compositions comprising a humectant, e.g., selected from glycerin, sorbitol, propylene glycol, polyethylene glycol, xylitol, and mixtures thereof, e.g. comprising at least 20%, e.g., 20-40%, e.g., 25-35% glycerin.
4.10. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from 0.3% to 4.5% by weight, e.g. 1-2% sodium lauryl sulfate (SLS); and/or a zwitterionic surfactant, for example a betaine surfactant, for example cocamidopropylbetaine, e.g. in an amount of from 0.1% to 4.5% by weight, e.g. 0.5-2% cocamidopropylbetaine.
4.11. Any of the preceding compositions further comprising a viscosity modifying amount of one or more of polysaccharide gums, for example xanthan gum or carrageenan, silica thickener, and combinations thereof.
4.12. Any of the preceding compositions comprising gum strips or fragments.
4.13. Any of the preceding compositions further comprising flavoring, fragrance and/or coloring.
4.14. Any of the foregoing compositions comprising an effective amount of one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.
4.15. Any of the foregoing compositions comprising an antibacterially effective amount of triclosan, e.g. 0.1-0.5%, e.g. 0.3%.
4.16. Any of the preceding compositions further comprising a whitening agent, e.g., a selected from the group consisting of peroxides, metal chlorites, perborates, percarbonates, peroxyacids, hypochlorites, and combinations thereof.
4.17. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);
4.18. Any of the preceding compositions further comprising an agent that interferes with or prevents bacterial attachment, e.g., solbrol or chitosan.
4.19. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate
4.20. Any of the preceding compositions further comprising a soluble calcium salt, e.g., selected from calcium sulfate, calcium chloride, calcium nitrate, calcium acetate, calcium lactate, and combinations thereof.
4.21. Any of the preceding compositions further comprising a physiologically or orally acceptable potassium salt, e.g., potassium nitrate or potassium chloride, in an amount effective to reduce dentinal sensitivity.
4.22. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of 30,000 to 1,000,000, e.g. 300,000 to 800,000, e.g., wherein the anionic polymer is 1-5%, e.g., 2%, of the weight of the composition.

4.23. Any of the preceding compositions further comprising a breath freshener, fragrance or flavoring.

4.24. Any of the foregoing compositions, wherein the pH of the composition is 7 to 11, or 9 to 11, or 8 to 10 or 8 to 9.

4.25. Any of the foregoing compositions in the form of an oral gel, wherein the amino acid is lysine and the TBZC and lysine form a zinc amino acid halide complex in an amount to provide 0.1-8%, e.g., 0.5% zinc by weight, and further comprising humectant, e.g., sorbitol, propylene glycol and mixtures thereof, e.g., in an amount of 45-65%, e.g., 50-60%, thickeners, e.g., cellulose derivatives, e.g., selected from carboxymethyl cellulose (CMC), trimethyl cellulose (TMC) and mixtures thereof, e.g., in an amount of 0.1-2%, sweetener and/or flavorings, and water, e.g., an oral gel comprising

| Ingredients | Weight % |
| --- | --- |
| Sorbitol | 40-60%, e.g., 50-55% |
| TBZC-Lys | to provide 0.1-2% Zn, e.g 0.5% Zn |
| Cysteine | 0.02-0.5%, e.g., 0.1% |
| Carboxymethyl cellulose (CMC) and Trimethyl cellulose (TMC) | 0.5-1%, e.g., 0.7% |
| Flavoring and/or sweetener | 0.01-1% |
| Propylene Glycol | 1-5%, e.g., 3.00% |

4.26. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

Also provided are methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of a composition, e.g., any of Composition 4, et seq. to the teeth, and optionally then rinsing with water or aqueous solution sufficient to trigger precipitation of an insoluble zinc-containing precipitate Also provided is a method of making an oral care composition comprising (i) a TBZH-AA or TBZH-TAG complex and (ii) cysteine in free or orally acceptable salt form, e.g., any of Composition 4, et seq. comprising combining (i) combining a TBZH, an amino acid source, and a chloride source (wherein the chloride source can be part of the zinc ion source, the amino acid source, or a hydrochloric acid), in a fluid (e.g., aqueous) medium, optionally isolating the complex thus formed in solid form, combining the complex with cysteine, or (ii) combining a TBZH-AA complex and cysteine. The TBZH-AA or TBZH-TAG complex and cysteine can be combined with an oral care base, e.g., a dentifrice or mouthwash base.

For example, in various embodiments, provided are methods to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of Compositions 4, et seq. as described above to the oral cavity of a person in need thereof, e.g., one or more times per day. Also provided are Compositions 4, et seq. for use in any of these methods.

Also provided is the use of (i) a TBZH-AA or TBZH-TAG complex, and (ii) cysteine in free or orally acceptable salt form in the manufacture of an oral care composition, e.g., in accordance with any of Compositions 4, et seq.

Also provided is the use of (i) a TBZH-AA or TBZH-TAG complex, and (ii) cysteine in free or orally acceptable salt form, to reduce and inhibit acid erosion of the enamel, clean the teeth, reduce bacterially-generated biofilm and plaque, reduce gingivitis, inhibit tooth decay and formation of cavities, and/or reduce dentinal hypersensitivity.

Also provided is the use of cysteine in free or orally acceptable salt form to stabilize a TBZH-AA complex. In one embodiment, the TBZH-AA or TBZH-TAG complex is prepared at room temperature by mixing the precursors in an aqueous solution. The in situ formation provides ease of formulation. The precursors can be used instead of first having to form the salt. In another embodiment, the water permitting formation of the salt from the precursor comes from water (e.g., rinsing water, saliva or sweat, depending on the application) that comes into contact with the composition in the course of use.

Because the number of moles or weight percent of various zinc salts and complexes herein will vary based on the particular salt or complex form, we frequently refer herein to the amount of total zinc in the formulation by weight or by molar amount, irrespective of its salt or complex form. In some embodiments, the total amount of zinc in the composition is 0.05 to 8% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition. For example, in some embodiments, the total amount of zinc in the composition may be 2-3% or 1%.

In certain embodiments, the composition is anhydrous. By anhydrous, there is less than 5% by weight water, optionally less than 4, less than 3, less than 2, less than 1, less than 0.5, less than 0.1 down to 0% by weight water. When provided in an anhydrous composition, precursors of the TBZH-AA complex, e.g., TBZC and lysine hydrochloride, will not significantly react. When contacted with a sufficient amount of water, the precursors will then react to form the desired salt, e.g., TBZC-Lys, which upon further dilution with use forms the desired precipitate on the skin or teeth.

Amino Acids:

The amino acid in the TBZH-AA complex can a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In a particular embodiment, the basic amino acid is lysine. The basic amino acids for use in making zinc amino acid halide complex are generally provided in the form of the halide acid addition salt, e.g., a hydrochloride.

The compositions also comprise cysteine in free or orally or cosmetically acceptable salt form. By "orally or cosmetically acceptable salt form" is meant a salt form which is safe for administration to the oral cavity or skin respectively in the concentrations provided, and which does not interfere with the biological activity of the zinc. In a particular embodiment, the cysteine is administered in free form. Wherever weights are given for amounts of amino acids in formulations herein, the weights are generally provided in terms of the weight of the free acid unless otherwise noted. In one embodiment, the cysteine salt can be an acid, such as cysteine hydrohalide (for example, cysteine hydrochloride).

In compositions comprising an orally or cosmetically acceptable carrier, the carrier represents all other materials in the composition other than TBZH-AA or TBZH-TAG complex (including precursors) and the cysteine. The amount of carrier is thus the amount to reach 100% by adding to the weight of TBZH-AA or TBZH-TAG complex (including precursors) and the protein. By "orally acceptable carrier" is meant a carrier which is suitable for use in an oral care product, containing ingredients which are generally recognized as safe for use in amounts and concentrations as provided in a dentifrice or mouth rinse, for example. By "cosmetically acceptable carrier" is meant a carrier which is suitable for use in a product for topical use on the skin, containing ingredients which are generally recognized as safe for use in amounts and concentrations as provided in a liquid hand soap or body wash, or in an antiperspirant product, for example. Excipients for use in the compositions thus may include for example excipients which are "Generally Recognized as Safe" (GRAS) by the United States Food and Drug Administration.

Personal Care Formulations:

The term "cosmetically acceptable carrier" thus refers to any formulation or carrier medium that provides the appropriate delivery of an effective amount of the complex as defined herein, does not interfere with the effectiveness of the biological activity of the zinc, and is suitable and nontoxic for topical administration to the skin. Representative carriers include water, oils, both vegetable and mineral, soap bases, cream bases, lotion bases, ointment bases and the like, particularly aqueous detergent carriers, for example liquid hand soaps or body washes. In one embodiment, the aqueous soap bases are free of or contain less than one percent of anionic surfactants. In another embodiment, the cosmetically acceptable carrier contains topically acceptable quaternary ammonium compounds. They may additionally include buffers, preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, and other conventional components of topical formulations as are known in the art.

In some cases, the personal care compositions comprise oils or moisturizers, which may not be water soluble and may be delivered in an emulsion system, wherein the zinc-lysine complex would be in the water phase of the emulsion. Surfactants for the emulsion formulations may comprise a combination of nonionic surfactants, for example, one or more surfactants selected from the group consisting of: (i) lipophilic surfactants, e.g., having an HLB value of 8 or lower, for example sorbitan-fatty acid esters, such as sorbitan oleates, for example, sorbitan sesquioleate; and (ii) hydrophilic surfactants, e.g., having an HLB of greater than 8, particularly a. di- or tri-alkanol amines, such as triethanol amine; b. polyethoxylated surfactants, for example polyethoxylated alcohols (esp. polyethoxylated polyols), polyethoxylated vegetable oils, and polyethoxylated silicones, e.g., polysorbate 80, dimethicone polyethylene oxide, and dimethylmethyl (polyethylene oxide) siloxane. For a water-in-oil emulsion, the overall HLB of the surfactant mixture is preferably 2-8, i.e., there is typically a higher proportion of lipophilic surfactant; whereas for an oil-in-water emulsion, the overall HLB of the surfactant mixture is preferably 8-16.

The personal care compositions may also comprise suitable antioxidants, substances known to inhibit oxidation. Antioxidants suitable for use in the compositions include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-fert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene. These materials are available from Ruger Chemical Co, (Irvington, N.J.). When the topical formulations contain at least one antioxidant, the total amount of antioxidant present is 0.001 to 0.5 weight %, preferably 0.05 to 0.5 weight %, more preferably 0.1%.

The personal care compositions may also comprise suitable preservatives. Preservatives are compounds added to a formulation to act as an antimicrobial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. When the topical formulations contain at least one preservative, the total amount of preservative present is 0.01 to 0.5 weight %, preferably from 0.1 to 0.5%, more preferably 0.03 to 0.15 weight %.

The personal care compositions may also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N, N',N'-tetraacetic acid (EGTA) and 8-Amino-2-[(2-amino-5-methylphenoxy)methyl]-6-methoxyquinoline-$N_5$N,N',N'-tetraacetic acid, tetrapotassium salt (QUIN-2). Preferably the chelating agents are EDTA and citric acid. These materials are available from Spectrum Chemicals. When the topical formulations contain at least one chelating agent, the total amount of chelating agent present is 0.005% to 2.0% by weight, preferably from 0.05% to 0.5 weight %, more preferably 0.1% by weight. Care must be taken that the chelators do not interfere with the zinc complex, for example by binding zinc, but in the formulations tested, low levels of EDTA, for example, have not presented problems.

The personal care compositions may also comprise suitable pH adjusting agents and/or buffers to adjust and maintain the pH of the formulation to a suitable range, e.g., pH 6-8 or approximately neutral pH.

The personal care compositions may also comprise suitable viscosity increasing agents. These components are diffusible compounds capable of increasing the viscosity of a polymer-containing solution through the interaction of the agent with the polymer. CARBOPOL ULTREZ 10 may be used as a viscosity-increasing agent. These materials are available from Lubrizol, Cleveland, Ohio. When the topical formulations contain at least one viscosity increasing agent, the total amount of viscosity increasing agent present is 0.25% to 5.0% by weight, preferably from 0.25% to 1.0 weight %, and more preferably from 0.4% to 0.6% by weight.

Liquid forms, such as lotions suitable for topical administration or suitable for cosmetic application, may include a suitable aqueous or nonaqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like.

Topical treatment regimens can comprise applying the composition directly to the skin at the application site, from one to several times daily, and washing with water to trigger precipitation of the zinc oxide on the skin.

Formulations can be used to treat, ameliorate or prevent conditions or symptoms associated with bacterial infections, acne, inflammation and the like.

Oral Care Formulations:

The oral care compositions, e.g., Composition 4, et seq. may comprise various agents which are active to protect and enhance the strength and integrity of the enamel and tooth structure and/or to reduce bacteria and associated tooth decay and/or gum disease, including or in addition to the TBZH-AA complexes. Effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., 0.1 to 20 wt % (expressed as weight of free base), e.g., 1 to 10 wt % for a consumer toothpaste or 7 to 20 wt % for a professional or prescription treatment product. Fluoride where present may be present at levels of, e.g., 25 to 25,000 ppm, for example 750 to 2,000 ppm for a consumer toothpaste, or 2,000 to 25,000 ppm for a professional or prescription treatment product. Levels of antibacterial agents will vary similarly, with levels used in toothpaste being e.g., 5 to 15 times greater than used in mouthrinse. For example, a triclosan toothpaste may contain 0.3 wt % triclosan.

The oral care compositions may further include one or more fluoride ion sources, e.g., soluble fluoride salts. A wide variety of fluoride ion-yielding materials can be employed as sources of soluble fluoride in the present compositions. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition may also contain a source of fluoride ions or fluorine-providing ingredient in amounts sufficient to supply 25 ppm to 25,000 ppm of fluoride ions, generally at least 500 ppm, e.g., 500 to 2000 ppm, e.g., 1000 to 1600 ppm, e.g., 1450 ppm. The appropriate level of fluoride will depend on the particular application. A toothpaste for general consumer use would typically have 1000 to 1500 ppm, with pediatric toothpaste having somewhat less. A dentifrice or coating for professional application could have as much as 5,000 or even 25,000 ppm fluoride. Fluoride ion sources may be added to the compositions at a level of 0.01 wt. % to 10 wt. % in one embodiment or 0.03 wt. % to 5 wt. %, and in another embodiment 0.1 wt. % to 1 wt. % by weight of the composition in another embodiment. Weights of fluoride salts to provide the appropriate level of fluoride ion will obviously vary based on the weight of the counterion in the salt.

Abrasives:

The oral care compositions, e.g. Composition 4 et seq. may include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Other silica abrasive polishing materials useful herein, as well as the other abrasives, generally have an average particle size ranging 0.1 to 30 microns, 5 to 15 microns. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. In certain embodiments, abrasive materials useful in the practice of the oral care compositions include silica gels and precipitated amorphous silica having an oil absorption value of less than 100 cc/100 g silica and in the range of 45 cc/100 g to 70 cc/100 g silica. Oil absorption values are measured using the ASTA Rub-Out Method D281. In certain embodiments, the silicas are colloidal particles having an average particle size of 3 microns to 12 microns, and 5 to 10 microns. Low oil absorption silica abrasives particularly useful in the compositions are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging 7 to 10 microns in diameter, and an oil absorption of less than 70 cc/100 g of silica is an example of a low oil absorption silica abrasive useful in the composition.

Foaming Agents:

The oral care compositions also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the composition. Polyoxyethylene is also commonly known as polyethylene glycol ("PEG") or polyethylene oxide. The polyoxyethylenes suitable for this composition will have a molecular weight of 200,000 to 7,000,000. In one embodiment the molecular weight will be 600,000 to 2,000,000 and in another embodiment 800,000 to 1,000,000. Polyox® is the trade name for the high molecular weight polyoxyethylene produced by Union Carbide. The polyoxyethylene may be present in an amount of 1% to 90%, in one embodiment 5% to 50% and in another embodiment 10% to 20% by weight of the oral care carrier component of the oral care compositions. Where present, the amount of foaming agent in the oral care composition (i.e., a single dose) is 0.01 to 0.9% by weight, 0.05 to 0.5% by weight, and in another embodiment 0.1 to 0.2% by weight.

Surfactants:

The compositions may contain anionic, cationic, nonionic and/or zwitterionic surfactants.

i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate, ii. higher alkyl sulfates, such as sodium lauryl sulfate, iii. higher alkyl-ether sulfates, e.g., of formula $CH_3(CH_2)_m CH_2(OCH_2CH_2)_n OSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2 OSO_3Na)$.

iv. higher alkyl aryl sulfonates such as sodium dodecyl benzene sulfonate (sodium lauryl benzene sulfonate)

v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at 0.3% to 4.5% by weight, e.g., 1.5%. The compositions may optionally contain mixtures of surfactants, e.g., comprising anionic surfactants and other surfactants that may be anionic, cationic, zwitterionic or nonionic. Generally, surfactants are those which are reasonably stable throughout a wide pH range. In certain embodiments, the anionic surfactants useful herein include the water-soluble salts of alkyl sulfates having 10 to 18 carbon atoms in the alkyl radical and the water-soluble salts of sulfonated monoglycerides of fatty acids having 10 to 18 carbon atoms. Sodium lauryl sulfate, sodium lauroyl sarcosinate and sodium coconut monoglyceride sulfonates are examples of anionic surfactants of this type. In a particular embodiment, the composition, e.g., Composition 4, et seq., comprises sodium lauryl sulfate.

The surfactant or mixtures of compatible surfactants can be present in the composition in 0.1% to 5%, in another embodiment 0.3% to 3% and in another embodiment 0.5% to 2% by weight of the total composition.

Note that care must be taken that the anionic surfactants do not interfere with TBZH-AA complex or with the activity of the zinc. At relatively low levels and in a relatively low water formulation, the surfactants generally would not have major impact, but higher levels of anionic surfactant, particularly in aqueous formulations, anionic surfactants can be excluded. Cationic and/or nonionic surfactants may be utilized instead.

Tartar Control Agents:

In various embodiments, the compositions comprise an anticalculus (tartar control) agent. Suitable anticalculus agents include without limitation polyaminopropanesulfonic acid (AMPS), hexametaphosphate salts, zinc citrate trihydrate, polypeptides, polyolefin sulfonates, polyolefin phosphates, Such tarter control agents are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Flavoring Agents:

The oral care compositions may also include a flavoring agent. Flavoring agents which can be used in the composition include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of 0.1 to 5% by weight e.g. 0.5 to 1.5% by weight.

Polymers:

The oral care compositions may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of 0.5% to 5.0% by weight of the total composition are used.

The compositions may include an anionic polymer, for example in an amount of from 0.05 to 5%. Examples of the anionic polymer include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of 30,000 to 1,000,000, most preferably 300,000 to 800,000. These copolymers are available for example as Gantrez, e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging 0.05 to 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of 1,000 to 2,000,000. Another useful class of polymeric agents includes polyamino acids containing proportions of anionic surface-active amino acids such as aspartic acid, glutamic acid and phosphoserine.

The oral compositions may comprise significant levels of water. Water employed in the preparation of commercial oral compositions should be deionized and free of organic impurities. The amount of water in the compositions includes the free water which is added plus that amount which is introduced with other materials.

Humectants:

Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerine, sorbitol, xylitol, propylene glycol as well as other polyols and mixtures of these humectants. In one embodiment, the principal humectant is glycerin, which may be present at levels of greater than 25%, e.g. 25-35% 30%, with 5% or less of other humectants.

Other Optional Ingredients:

In addition to the above-described components, the oral care embodiments can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents.

Unless stated otherwise, all percentages of composition components given in this specification are by weight based on a total composition or formulation weight of 100%.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the composition extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Example 1

Turbidity study of solutions: Turbidity measurements are conducted by Turbiscan (Formulaction Inc, Davie, Fla.). The measurement of this instrument is performed by sending out a light beam through the cell with sample solution and detecting the photons that cross the solution without being diffused. The result is shown in percent transmission—a higher percent transmission corresponds to a clearer solution, and a decrease of percent transmission indicates the formation of precipitate in solution. The temperature of the instrument is set at 37° C. Turbidity is measured in a one minute interval for 30 minutes under this temperature. All dilutions are freshly prepared before measurements.

In the following experiments, three different Zinc Lysine mixture solution with 0.5% Cysteine is prepared:

1) TBZC-Lys-Cys:

7.3 g (0.05 mol) of Lysine is dissolved to 50 ml DI water. To this lysine solution, 2.8 g (0.005 mol) of TBZC is added. The Zn/Lysine ratio is 1:2. Allow the mixture to be stirred at room temperature (ROOM TEMPERATURE) over a weekend. Then, the unreacted TBZC is removed by centrifuging followed by filtering the solution through 0.45 μm membrane. The pH of supernatant is 10.1. To 19.9 g of this solution, 0.1 g of Cysteine powder is added, and the final solution is transparent and yellowish. We notice the solution become turbid after aging 24 h at ROOM TEMPERATURE.

2) TBZC-LysHCl-Cys:

9.13 g (0.05 mol) of LysineHCl is dissolved to 50 m DI water. To this LysineHCl solution, 2.76 g (0.005 mol) of TBZC is added. The Zn/Lysine ratio is 1:2. Allow the mixture to be stirred at ROOM TEMPERATURE over weekend. Then, the unreacted TBZC is removed by centrifuging followed by filtering the solution through 0.45 μm membrane. The pH of supernatant is 6. To 19.9 g of this solution, 0.1 g of Cysteine powder is added. However, white precipitate is formed, the solution is not transparent.

3) ZnCl$_2$-Lys-Cys:

7.3 g (0.05 mol) of Lysine is dissolved to 50 ml DI water. To this lysine solution, 3.4 g (0.025 mol) of ZnCl$_2$ is added. The Zn/Lysine ratio is 1:2. Allow the mixture to be stirred at ROOM TEMPERATURE over weekend. Then, the unreacted ZnCl$_2$ is removed by centrifuging followed by filtering the solution through 0.45 μm membrane. The pH of supernatant is 7. To 19.9 g of this solution, 0.1 g of Cysteine powder is added to see white precipitate formed, the solution is not transparent.

The addition of Cysteine amino acid to TBZC-LysHCl solution will cause immediate precipitation and the precipitate cannot be further dissolved. Only TBZC-Lys solution keeps transparent after the addition of Cysteine. Therefore, a turbidity study is conducted with TBZC-Lys and TBZC-Lys-Cys solution. Both TBZC-Lys and TBZC-Lys-Cys solution is diluted into 2 fold, 4 fold, 8 fold, 16 fold and 32 fold dilutions.

The results are in Table A. The 2 fold dilution of TBZC-Lys is stable during the measurement period. Precipitate is formed instantly when this solution is further diluted to 4 fold. The formation of precipitate is instant and settles down to the bottle after 10 mins. Immediate precipitation is also observed in 8 fold dilution, compared with the initial % transmission to 4 fold dilution, the smaller number suggests that more precipitate is formed. A faster sedimentation of precipitate in 8 fold dilution (about 5 mins) is observed. 16 fold dilution has the same behavior as 4 fold and 8 fold dilution but forms more precipitate and has quicker sedimentation. Compared to 16 fold dilution, 32 fold dilution also forms precipitate instantly but the amount is less. The % transmission of 32 fold dilution keeps at about 35% which means no sedimentation occurs during the measurement period.

After the addition of 0.5% Cysteine into TBZC-Lys system, 2 fold and 4 fold dilutions of this new mixture solution are both stable during 30 mins measurement period. Instant precipitation is observed in 8 fold, 16 fold and 32 fold dilutions. And these dilutions show the same behavior as TBZC-Lys, however, the amount of precipitate formed are all less than the solution without addition of Cysteine.

TABLE A

| | 2 fold dilution | | 4 fold dilution | | 8 fold dilution | | 16 fold dilution | | 32 fold dilution | |
|---|---|---|---|---|---|---|---|---|---|---|
| t(mm) | t(sec) | T(t) 5 mm-45 mm (%) | t(sec) | T(t) 5 mm-45 mm (%) | t(sec) | T(t) 5 mm-45 mm (%) | t(sec) | T(t) 5 mm-45 mm (%) | t(sec) | T(t) 5 mm-45 mm (%) |
| 0 | 0 | 89.86 | 0 | 90.49 | 0 | 39.23 | 0 | 23.95 | 0 | 29.19 |
| 1 | 60 | 89.97 | 60 | 90.53 | 60 | 47.74 | 60 | 35.48 | 60 | 31.56 |
| 2 | 120 | 89.95 | 120 | 90.5 | 120 | 59.81 | 120 | 44.2 | 120 | 40.42 |
| 3 | 180 | 89.93 | 180 | 90.48 | 180 | 62.41 | 180 | 46.42 | 180 | 41.86 |
| 4 | 240 | 89.91 | 240 | 90.47 | 240 | 63.19 | 240 | 46.5 | 240 | 42.45 |
| 5 | 300 | 89.91 | 300 | 90.45 | 300 | 63.07 | 300 | 45.98 | 300 | 42.56 |
| 6 | 360 | 89.89 | 360 | 90.43 | 360 | 62.51 | 360 | 45.36 | 360 | 42.46 |
| 7 | 420 | 89.89 | 420 | 90.41 | 420 | 61.62 | 420 | 44.84 | 420 | 42.42 |
| 8 | 480 | 89.87 | 480 | 90.4 | 480 | 60.67 | 480 | 44.34 | 480 | 42.49 |
| 9 | 540 | 89.87 | 540 | 90.37 | 540 | 59.83 | 540 | 44.06 | 540 | 42.61 |
| 10 | 600 | 89.86 | 600 | 90.36 | 600 | 59.06 | 600 | 43.87 | 600 | 42.79 |
| 11 | 660 | 89.86 | 660 | 90.32 | 660 | 58.24 | 660 | 43.74 | 660 | 43.06 |
| 12 | 720 | 89.85 | 720 | 90.3 | 720 | 57.56 | 720 | 43.62 | 720 | 42.54 |
| 13 | 780 | 89.84 | 780 | 90.3 | 780 | 56.86 | 780 | 43.62 | 780 | 43.13 |
| 14 | 840 | 89.84 | 840 | 90.27 | 840 | 56.32 | 840 | 43.55 | 840 | 43.54 |
| 15 | 900 | 89.83 | 900 | 90.23 | 900 | 55.87 | 900 | 43.51 | 900 | 44.12 |
| 16 | 960 | 89.84 | 960 | 90.21 | 960 | 55.5 | 960 | 43.61 | 960 | 44.66 |
| 17 | 1020 | 89.83 | 1020 | 90.18 | 1020 | 55.17 | 1020 | 43.88 | 1020 | 45.16 |
| 18 | 1080 | 89.84 | 1080 | 90.14 | 1080 | 54.88 | 1080 | 44.11 | 1080 | 45.6 |
| 19 | 1140 | 89.82 | 1140 | 90.12 | 1140 | 54.64 | 1140 | 44.37 | 1140 | 46.16 |
| 20 | 1200 | 89.81 | 1200 | 90.08 | 1200 | 54.41 | 1200 | 44.59 | 1200 | 46.62 |
| 21 | 1260 | 89.82 | 1260 | 90.05 | 1260 | 54.24 | 1260 | 44.86 | 1260 | 47.06 |
| 22 | 1320 | 89.82 | 1320 | 90 | 1320 | 54.14 | 1320 | 45.32 | 1320 | 47.56 |
| 23 | 1380 | 89.82 | 1380 | 89.95 | 1380 | 53.86 | 1380 | 45.63 | 1380 | 48.03 |
| 24 | 1440 | 89.81 | 1440 | 89.92 | 1440 | 53.84 | 1440 | 46.03 | 1440 | 48.47 |
| 25 | 1500 | 89.81 | 1500 | 89.87 | 1500 | 53.75 | 1500 | 46.42 | 1500 | 48.91 |
| 26 | 1560 | 89.82 | 1560 | 89.83 | 1560 | 53.67 | 1560 | 46.83 | 1560 | 49.25 |
| 27 | 1620 | 89.81 | 1620 | 89.77 | 1620 | 53.62 | 1620 | 47.32 | 1620 | 49.58 |
| 28 | 1680 | 89.82 | 1680 | 89.72 | 1680 | 53.23 | 1680 | 47.71 | 1680 | 49.91 |
| 29 | 1740 | 89.81 | 1740 | 89.68 | 1740 | 52.7 | 1740 | 48.04 | 1740 | 50.23 |
| 30 | 1800 | 89.82 | 1800 | 89.61 | 1800 | 53.17 | 1800 | 48.5 | 1800 | 50.47 |

Example 2

In the following experiments, five different TBZC-Lysine-Cysteine mixture solutions are prepared:

1) TBZC-Lys-Cys with 0.05% Cysteine by Weight:

7.3 g (0.05 mol) of Lysine is dissolved to 50 ml DI water. To this lysine solution, 2.8 g (0.005 mol) of TBZC is added. The Zn/Lysine ratio is 1:2. Allow the mixture to be stirred at ROOM TEMPERATURE over 4 hours. Then, the unreacted TBZC is removed by centrifuging followed by filtering the solution through 0.451 m membrane. The pH of supernatant is 10.1. To 20 g of this solution, 0.01 g of Cysteine powder is added, and the final solution is transparent and yellow. However, after aging at room temperature for about 24 hours, the solution becomes turbid.

2) TBZC-Lys-Cys with 0.075% Cysteine by Weight:

7.3 g (0.05 mol) of Lysine is dissolved to 50 ml DI water. To this lysine solution, 2.8 g (0.005 mol) of TBZC is added. The Zn/Lysine ratio is 1:2. Allow the mixture to be stirred at ROOM TEMPERATURE over 4 hours. Then, the unreacted TBZC is removed by centrifuging followed by filtering the solution through 0.45 μm membrane. The pH of supernatant is 10.1. To 19.985 g of this solution, 0.015 g of Cysteine powder is added, and the final solution is transparent and yellow. However, after aging at room temperature for about 24 hours, the solution becomes turbid.

3) TBZC-Lys-Cys with 0.09% Cysteine by Weight:

7.3 g (0.05 mol) of Lysine is dissolved to 50 ml DI water. To this lysine solution, 2.8 g (0.005 mol) of TBZC is added. The Zn/Lysine ratio is 1:2. Allow the mixture to be stirred at ROOM TEMPERATURE over 4 hours. Then, the unreacted TBZC is removed by centrifuging followed by filtering the solution through 0.451 m membrane. The pH of supernatant is 10.1. To 19.982 g of this solution, 0.018 g of Cysteine powder is added, and the final solution is transparent and yellow. However, after aging at room temperature for about 24 hours, the solution becomes turbid.

4) TBZC-Lys-Cys with 0.1% Cysteine by Weight:

7.3 g (0.05 mol) of Lysine is dissolved to 50 ml DI water. To this lysine solution, 2.8 g (0.005 mol) of TBZC is added. The Zn/Lysine ratio is 1:2. Allow the mixture to be stirred at ROOM TEMPERATURE over 4 hours. Then, the unreacted TBZC is removed by centrifuging followed by filtering the solution through 0.45 μm membrane. The pH of supernatant is 10.1. To 19.98 g of this solution, 0.02 g of Cysteine powder is added, and the final solution is transparent and yellow. However, after aging at room temperature for about 24 hours, the solution becomes turbid.

5) TBZC-Lys-Cys with 0.15% Cysteine by Weight:

7.3 g (0.05 mol) of Lysine is dissolved to 50 ml DI water. To this lysine solution, 2.8 g (0.005 mol) of TBZC is added. The Zn/Lysine ratio is 1:2. Allow the mixture to be stirred at ROOM TEMPERATURE over 4 hours. Then, the unreacted TBZC is removed by centrifuging followed by filtering the solution through 0.451 μm membrane. The pH of supernatant is 10.1. To 19.97 g of this solution, 0.03 g of Cysteine powder is added, and the final solution is transparent and yellow. However, after aging at room temperature for about 24 hours, the solution becomes turbid.

Upon addition of Cysteine, the TBZC-Lys solutions with varied amounts of Cysteine remain transparent. The instrument and procedures used in this experiment is the same as those described in Example 1. All three solutions of TBZC-Lys-Cys with differing amounts of cysteine are diluted into 2 fold, 4 fold, 8 fold, 16 fold, and 32 fold dilutions.

Results

Table B shows the results for the solutions containing 0.05% Cysteine. As can be seen, the 2 fold diluted solution is stable during the 20 minute measurement period. Instant precipitation occurs for the 4 fold, 8 fold, 16 fold and 32 fold diluted solutions. For the 4 fold diluted sample, the precipitation is so quick that it settles down to the bottom of the bottle after 4 minutes. The initial % transmission of the 8 fold dilution, as compared to the 4 fold dilution, is smaller—suggesting that more precipitate is formed. Sedimentation of the precipitate is complete at around 6 minutes for the 8 fold dilution. The 16 fold dilution has the same behavior as the 8 fold dilution but forms a precipitate in an intermediate amount to the 4 fold and 8 fold dilutions. Furthermore, the 16 fold dilution has a slower sedimentation rate than the 4 fold and 8 fold (about 8 minutes). Compared to the 16 fold dilution, the 32 fold dilution also forms a precipitate instantly but the amount is less. The 32 fold dilution forms a precipitate so quickly that it begins to settle down to the bottom of the bottle after about 4 minutes.

The initial pH of the diluted samples containing 0.05% cysteine by weight, as can be seen in Table 1, range from 9.7 to 10.1, with the most diluted sample having the lowest pH. The two fold dilution appears clear. The rest of the dilutes contain a white precipitate. As can be seen in Table 2, upon changing the pH of the diluted solutions containing 0.05% cysteine to a pH similar to sweat (around 5.5), the precipitate in all of the solutions is dissolved, as indicated by the transparency of the solutions.

As can be seen in Table C for the solutions containing 0.075% cysteine by weight, the 2 fold dilution remains stable at 90%. In other words, during the 20 minute measuring period, the 2 fold dilution does not form a precipitate. The 4 fold, 8 fold, 16 fold and 32 fold dilutions form a white precipitate instantly. The 4 fold dilution continuously forms precipitate throughout the measuring period. The final percent transmission of the 4 fold dilution is 24.8%. The 8 fold, 16 fold and 32 fold dilutions behave very similarly during the 20 minute period. The 8 fold dilution forms the most initial precipitation of all the samples with an initial percent transmission of 18.07%. Over time, the precipitate settles to the bottom of the test-tube which is reflected by the increase in percent transmission. The 16 fold dilution forms an instantaneous precipitate in an amount that is intermediate to the 8 fold and 32 fold dilutions. Over time, the precipitate of the 16 and 32 fold dilutions settles to the bottom of the test-tube which is reflected by the increase in percent transmission.

The initial pH of the diluted samples containing 0.075% cysteine by weight, as can be seen in Table 3, range from 9.66-10.16 with the most diluted samples having the lowest pH. All of the diluted samples contain a white precipitate. As can be seen in Table 4, upon changing the pH of the diluted samples containing 0.075% Cysteine to a pH similar to that of sweat, none of the dilutions contain a precipitate.

The 2 fold diluted sample containing 0.09% Cysteine by weight, as shown in Table D, remains stable at around 89% transmission. In other words, during the 20 minute measuring period, the 2 fold dilution does not form a precipitate. The 4 fold, 8 fold, 16 fold and 32 fold dilutions form a white precipitate instantly and behave very similarly during the measuring period. The 4 fold dilution continuously forms precipitate throughout the measuring period. The final percent transmission of the 4 fold dilution is 30.59%. The 4 fold dilution forms the most initial precipitation of all the samples, followed by the 8 fold dilution, the 16 fold dilution and the 32 fold dilution, respectively in that order.

The initial pH of the diluted samples containing 0.09% cysteine by weight, as can be seen in Table 5, range from 9.8 to 10.2. All of the diluted samples contain a white precipitate. As can be seen in Table 6, upon changing the pH of the diluted samples containing 0.09% Cysteine to a pH similar to that of sweat, none of the dilutions contain a precipitate.

Table E shows that for the solutions containing 0.1% cysteine, the 2 fold and 4 fold diluted solutions are both stable throughout the 20 minute measurement period. Instant precipitation is observed in the 8 fold, 16 fold, and 32 fold dilutions. The 8 fold dilution produces a greater amount of precipitate than the 2 fold and 4 fold dilutions. The 8 fold dilution has an initial % transmission of 70% and after about 7 minutes, it remains at around 77% for the rest of the 20 minute time period. This implies that no further sedimentation occurs after around 7 minutes for the 8 fold dilution. The 16 fold dilution produces the greatest amount of precipitate, although it is still less than the 8 fold and 16 fold dilutions of the 0.05% cysteine solutions. The 32 fold dilution also forms a precipitate instantly but the amount is less than the 16 fold dilution. The % transmission of the 32 fold dilution keeps at about 65% which means that no sedimentation occurs during the measurement period.

The initial pH of the dilutions containing 0.1% cysteine by weight, as can be seen in Table 7, range from 9.70 to 10.00, with the most diluted sample having the lowest pH. All of the dilutions have a white precipitate. As can be seen in Table 8, upon changing the pH of the diluted solutions containing 0.1% cysteine to a pH similar to sweat (around 5.5), a precipitate is present in all of the solutions. (The 32 fold dilution appears to not have a precipitate initially, but after letting the solution sit overnight, a precipitate settles to the bottom of the test-tube.) The two fold dilution contains the most precipitate, and in the order of the dilutions, the rest of the diluted samples contain less and less precipitate.

Table F shows that for the solutions containing 0.15% cysteine, all of the dilutions experience instant precipitation. The 2 fold dilutions remains steady at around 65.5% transmission during the measurement period. The 8 fold and 32 fold dilutions have very similar initial percent transmissions, 19.02% for the 8 fold dilution and 19.97% for the 32 fold dilution. The 4 fold and 16 fold dilutions also have very similar initial percent transmissions, 25.9% for the 4 fold dilution and 24.82% for the 16 fold dilution. During the measurement period, the percent transmission of the 4 fold dilution increases at the beginning but after about 3 minutes it decreases for the rest of the time period. By the end of the 20 minute measurement period, the 4 fold dilution has the lowest percent transmission, followed by the 8 fold dilution, then the 16 fold dilution, then the 32 fold dilution, and finally the 2 fold dilution has the highest percent transmission.

The initial pH of the diluted samples containing 0.15% Cysteine by weight, as can be seen in Table 9, range from 9.63 to 10.21. All of the diluted samples contain a white precipitate. As can be seen in Table 10, upon changing the pH of the diluted samples containing 0.15% Cysteine to a pH similar to that of sweat, all of the dilutions containing a cloudy white precipitate, although the 32 fold dilution has little precipitate.

TABLE 1

Initial pH of Diluted Samples of TBZC-Lys-Cys with 0.05% Cysteine

| Dilution | 2x | 4x | 8x | 16x | 32x |
|---|---|---|---|---|---|
| pH | 10.1 | 10 | 10 | 9.9 | 9.7 |
| Observations | Clear | Cloudy white ppt | Cloudy white ppt | Cloudy white ppt | Cloudy white ppt |

TABLE 2

Diluted Samples of TBZC-Lys-Cys with 0.05% Cysteine with a pH similar to that of Sweat

| Dilution | 2x | 4x | 8x | 16x | 32x |
|---|---|---|---|---|---|
| pH | 5.5 | 5.2 | 5.2 | 5.2 | 5.4 |
| Observations | Clear | Clear | Clear | Clear | Clear |

TABLE 3

Initial pH of diluted samples of TBZC-Lys-Cys with 0.075% Cysteine

| Dilution | 2x | 4x | 8x | 16x | 32x |
|---|---|---|---|---|---|
| pH | 10.2 | 10 | 10 | 9.9 | 9.7 |
| Observations | White precipitate | White precipitate | White precipitate | White precipitate | Very little white precipitate |

TABLE 4

Diluted samples of TBZC-Lyc-Cys with 0.075% Cysteine after adjustment to a pH similar to that of Sweat

| Dilution | 2x | 4x | 8x | 16x | 32x |
|---|---|---|---|---|---|
| pH | 5.5 | 5.5 | 5.5 | 5 | 5.5 |
| Observations | No precipitate | No precipitate | No precipitate | No precipitate | No precipitate |

TABLE 5

Initial pH of diluted samples of TBZC-Lys-Cys with 0.09% Cysteine

| Dilution | 2x | 4x | 8x | 16x | 32x |
|---|---|---|---|---|---|
| pH | 10.3 | 10.1 | 10 | 9.9 | 9.8 |
| Observations | Very little precipitate | White precipitate | White precipitate | White precipitate | White precipitate |

TABLE 6

Diluted samples of TBZC-Lyc-Cys with 0.09% Cysteine after adjustment to a pH similar to that of Sweat

| Dilution | 2x | 4x | 8x | 16x | 32x |
|---|---|---|---|---|---|
| pH | 5.5 | 5.5 | 5.5 | 5.5 | 5.4 |
| Observations | No precipitate | No precipitate | No precipitate | No precipitate | No precipitate |

TABLE 7

Initial pH of Diluted Samples of TBZC-Lys-Cys with 0.1% Cysteine

| Dilution | 2x | 4x | 8x | 16x | 32x |
|---|---|---|---|---|---|
| pH | 10 | 10 | 9.9 | 9.8 | 9.7 |
| Observations | No precipitate | No precipitate | Cloudy white ppt | Cloudy white ppt | Cloudy white ppt |

TABLE 8

Diluted Samples of TBZC-Lys-Cys with 0.1% Cysteine with a pH similar to that of Sweat

| Dilution | 2x | 4x | 8x | 16x | 32x |
|---|---|---|---|---|---|
| pH | 5.5 | 5.4 | 5.5 | 5.4 | 5.5 |
| Observations | Cloudy white ppt | Cloudy white ppt | Cloudy white ppt | Cloudy white ppt | Cloudy white ppt |

TABLE 9

Initial pH of Diluted Samples of TBZC-Lys-Cys with 0.15% Cysteine

| Dilution | 2x | 4x | 8x | 16x | 32x |
|---|---|---|---|---|---|
| pH | 10.2 | 10 | 9.9 | 9.6 | 9.8 |
| Observations | Cloudy white ppt | Cloudy white ppt | Cloudy white ppt | Cloudy white ppt | Very little ppt |

TABLE 10

Diluted Samples of TBZC-Lys-Cys with 0.15% Cysteine with a pH similar to that of Sweat

| Dilution | 2x | 4x | 8x | 16x | 32x |
|---|---|---|---|---|---|
| pH | 5.5 | 5.5 | 5.5 | 5.4 | 5.4 |
| Observations | Cloudy white ppt | Cloudy white ppt | Cloudy white ppt | Cloudy white ppt | Very little ppt |

TABLE 11

Varying pH ranges of precipitation in the TBZC-Lys-Cys system with respect to variable levels of cysteine.

| wt % Cysteine | 0.09 | 0.10 | 0.12 | 0.15 |
|---|---|---|---|---|
| initial pH | 8.7 | 8.7 | 8.7 | 8.5 |
| initial precipitation (μL HCl) | 60 | 50 | 50 | 40 |
| initial precipitation pH | 7.4 | 7.4 | 7.3 | 7.3 |
| clear solution (μL HCl) | 140 | 140 | 130 | 130 |
| clear solution pH | 5 | 5.2 | 5 | 5.1 |

TABLE B

Turbidity in Varied Dilutions of TBZC-Lys-Cys with 0.05% Cysteine over a span of 20 minutes

| | | 2 fold | 4 fold | 8 fold | 16 fold | 32 fold |
|---|---|---|---|---|---|---|
| t(min) | t(sec) | T(t) 5 mm-45 mm (%) | T(t) 5 mm-45 mm (%) | T(t) 5 mm-45 mm (%) | T(t) 5 mm-45 mm (%) | T(t) 5 mm-45 mm (%) |
| 0 | 0 | 88.44 | 43.91 | 31.41 | 33.09 | 42.25 |
| 1 | 60 | 88.47 | 57.06 | 46.19 | 49.56 | 63.31 |
| 2 | 120 | 88.47 | 62.2 | 53.92 | 56.48 | 67.88 |
| 3 | 180 | 88.47 | 64.25 | 57.02 | 59.9 | 68.8 |
| 4 | 240 | 88.48 | 64.71 | 58.58 | 61.9 | 68.99 |
| 5 | 300 | 88.48 | 64.31 | 59.37 | 63.12 | 68.9 |
| 6 | 360 | 88.47 | 63.28 | 59.72 | 63.94 | 68.75 |
| 7 | 420 | 88.48 | 62.08 | 59.72 | 64.46 | 68.66 |
| 8 | 480 | 88.47 | 60.87 | 59.65 | 64.83 | 68.52 |
| 9 | 540 | 88.47 | 59.45 | 59.56 | 65.14 | 68.39 |
| 10 | 600 | 88.46 | 58.15 | 59.39 | 65.4 | 68.28 |
| 11 | 660 | 88.48 | 56.91 | 59.17 | 65.57 | 68.16 |
| 12 | 720 | 88.47 | 55.76 | 58.92 | 65.65 | 68.07 |
| 13 | 780 | 88.46 | 54.59 | 58.64 | 65.66 | 68.03 |
| 14 | 840 | 88.44 | 53.62 | 58.3 | 65.64 | 67.97 |
| 15 | 900 | 88.41 | 52.67 | 57.94 | 65.58 | 67.91 |
| 16 | 960 | 88.38 | 51.67 | 57.57 | 65.49 | 67.88 |
| 17 | 1020 | 88.32 | 50.77 | 57.2 | 65.37 | 67.85 |
| 18 | 1080 | 88.25 | 49.97 | 56.89 | 65.26 | 67.81 |
| 19 | 1140 | 88.16 | 49.19 | 56.61 | 65.17 | 67.81 |
| 20 | 1200 | 88.02 | 48.44 | 56.34 | 65.07 | 67.77 |

TABLE C

Turbidity in Varied Dilutions of TBZC-Lys-Cys with 0.075% Cysteine over a span of 20 minutes

| | 2x | 4x | 8x | 16x | 32x |
|---|---|---|---|---|---|
| t(min) | T(t) 5 mm-45 mm (%) | T(t) 5 mm-45 mm (%) | T(t) 5 mm-45 mm (%) | T(t) 5 mm-45 mm (%) | T(t) 5 mm-45 mm (%) |
| 0 | 89.98 | 23.63 | 18.07 | 25.44 | 34.89 |
| 1 | 89.98 | 29.52 | 28.09 | 34.53 | 50.94 |
| 2 | 89.97 | 31.91 | 37.2 | 43.26 | 57.81 |
| 3 | 89.96 | 32.44 | 41.21 | 46.37 | 59.24 |
| 4 | 89.96 | 32.24 | 43.88 | 47.95 | 59.93 |
| 5 | 89.94 | 31.78 | 45.82 | 48.96 | 60.3 |
| 6 | 89.94 | 31.36 | 47.02 | 49.67 | 60.63 |
| 7 | 89.94 | 30.81 | 47.88 | 50.17 | 60.89 |
| 8 | 89.94 | 30.08 | 48.46 | 50.7 | 61.05 |
| 9 | 89.94 | 29.3 | 48.85 | 51.12 | 61.37 |
| 10 | 89.93 | 28.59 | 49.15 | 51.54 | 61.56 |
| 11 | 89.92 | 27.79 | 49.44 | 52.03 | 61.7 |
| 12 | 89.92 | 27.35 | 49.64 | 52.48 | 61.98 |
| 13 | 89.93 | 26.77 | 49.72 | 53 | 62.3 |
| 14 | 89.91 | 26.21 | 49.75 | 53.55 | 62.59 |
| 15 | 89.91 | 25.78 | 49.66 | 54.09 | 62.9 |
| 16 | 89.9 | 25.49 | 49.57 | 54.55 | 63.3 |
| 17 | 89.9 | 25.31 | 49.73 | 55.01 | 63.74 |
| 18 | 89.89 | 25.13 | 49.81 | 55.33 | 64.31 |
| 19 | 89.89 | 24.95 | 49.97 | 55.55 | 64.92 |
| 20 | 89.88 | 24.8 | 50.15 | 55.83 | 65.43 |

TABLE D

Turbidity in Varied Dilutions of TBZC-Lys-Cys with 0.09% Cysteine over a span of 20 minutes

| | 2x | 4x | 8x | 16x | 32x |
|---|---|---|---|---|---|
| t(min) | T(t) 5 mm-45 mm (%) | T(t) 5 mm-45 mm (%) | T(t) 5 mm-45 mm (%) | T(t) 5 mm-45 mm (%) | T(t) 5 mm-45 mm (%) |
| 0 | 86.99 | 25.67 | 26.45 | 30.04 | 34.38 |
| 1 | 89.13 | 30.62 | 29.94 | 36.6 | 48.5 |
| 2 | 89.15 | 34.09 | 32.81 | 40.23 | 51.34 |
| 3 | 89.13 | 34.78 | 34.64 | 41.97 | 52.27 |
| 4 | 89.11 | 35.3 | 35.69 | 42.88 | 52.45 |
| 5 | 89.08 | 35.16 | 36.15 | 43.28 | 52.5 |
| 6 | 89.07 | 34.55 | 36.16 | 43.42 | 52.4 |
| 7 | 89.07 | 34.06 | 36 | 43.48 | 52.31 |
| 8 | 89.05 | 33.45 | 35.62 | 43.49 | 52.19 |
| 9 | 89.05 | 32.9 | 35.38 | 43.46 | 52.15 |
| 10 | 89.03 | 32.55 | 35.2 | 43.42 | 52.18 |
| 11 | 89.02 | 32.16 | 34.91 | 43.35 | 52.15 |
| 12 | 89.03 | 31.89 | 34.78 | 43.43 | 52.22 |
| 13 | 89.02 | 31.7 | 34.55 | 43.36 | 52.27 |
| 14 | 89.01 | 31.48 | 34.41 | 43.22 | 52.39 |
| 15 | 89.01 | 31.39 | 34.38 | 43.11 | 52.36 |
| 16 | 89.01 | 31.13 | 34.44 | 43.06 | 52.38 |
| 17 | 89 | 30.88 | 34.32 | 43.17 | 52.4 |
| 18 | 89 | 30.74 | 34.14 | 43.1 | 52.43 |
| 19 | 88.98 | 30.5 | 34 | 42.96 | 52.56 |
| 20 | 88.99 | 30.59 | 33.89 | 42.7 | 52.68 |

TABLE E

Turbidity in Varied Dilutions of TBZC-Lys-Cys with 0.1% Cysteine over a span of 20 minutes

| t(min) | 2x T(t) 5 mm-45 mm (%) | 4x T(t) 5 mm-45 mm (%) | 8x T(t) 5 mm-45 mm (%) | 16x T(t) 5 mm-45 mm (%) | 32x T(t) 5 mm-45 mm (%) |
|---|---|---|---|---|---|
| 0 | 90.3 | 89.83 | 70.24 | 38.34 | 62.92 |
| 1 | 90.34 | 89.83 | 73.77 | 57.26 | 62.92 |
| 2 | 90.37 | 89.82 | 74.55 | 61.32 | 63.12 |
| 3 | 90.36 | 89.82 | 74.84 | 63.5 | 63.51 |
| 4 | 90.37 | 89.81 | 75.27 | 63.99 | 63.86 |
| 5 | 90.36 | 89.8 | 75.57 | 63.91 | 64.11 |
| 6 | 90.34 | 89.78 | 75.73 | 63.43 | 64.54 |
| 7 | 90.35 | 89.78 | 76.33 | 63.09 | 64.88 |
| 8 | 90.34 | 89.77 | 77 | 62.61 | 65.2 |
| 9 | 90.35 | 89.76 | 77.67 | 62.33 | 65.53 |
| 10 | 90.33 | 89.76 | 77.93 | 62.01 | 65.81 |
| 11 | 90.33 | 89.76 | 78.19 | 61.72 | 66.07 |
| 12 | 90.34 | 89.74 | 78.55 | 61.51 | 66.22 |
| 13 | 90.33 | 89.75 | 78.69 | 61.32 | 66.28 |
| 14 | 90.32 | 89.74 | 78.69 | 60.97 | 66.41 |
| 15 | 90.33 | 89.75 | 78.63 | 61.07 | 66.55 |
| 16 | 90.32 | 89.74 | 78.58 | 61.08 | 66.76 |
| 17 | 90.32 | 89.73 | 78.45 | 61.07 | 66.88 |
| 18 | 90.33 | 89.73 | 78.32 | 61.13 | 66.99 |
| 19 | 90.33 | 89.74 | 77.95 | 61 | 67.13 |
| 20 | 90.33 | 89.74 | 77.73 | 60.67 | 67.18 |

TABLE F

Turbidity in Varied Dilutions of TBZC-Lys-Cys with 0.15% Cysteine over a span of 20 minutes

| t(min) | 2x T(t) 5 mm-45 mm (%) | 4x T(t) 5 mm-45 mm (%) | 8x T(t) 5 mm-45 mm (%) | 16x T(t) 5 mm-45 mm (%) | 32x T(t) 5 mm-45 mm (%) |
|---|---|---|---|---|---|
| 0 | 63.82 | 25.9 | 19.02 | 24.82 | 19.97 |
| 1 | 65.7 | 40.28 | 29.82 | 29 | 46.46 |
| 2 | 65.7 | 47.4 | 32.23 | 33.41 | 48.07 |
| 3 | 65.7 | 48.33 | 32.79 | 35.89 | 48.12 |
| 4 | 65.71 | 48.12 | 32.95 | 37.53 | 48.14 |
| 5 | 65.69 | 47.31 | 33.11 | 38.55 | 48.18 |
| 6 | 65.66 | 46.1 | 33.09 | 39.09 | 48.25 |
| 7 | 65.62 | 44.81 | 33.1 | 39.42 | 48.3 |
| 8 | 65.56 | 43.45 | 33.24 | 39.54 | 48.36 |
| 9 | 65.48 | 42.16 | 33.29 | 39.59 | 48.46 |
| 10 | 65.47 | 40.94 | 33.43 | 39.58 | 48.53 |
| 11 | 65.38 | 39.77 | 33.47 | 39.47 | 48.65 |
| 12 | 65.32 | 38.76 | 33.67 | 39.44 | 48.75 |
| 13 | 65.28 | 37.95 | 33.89 | 39.4 | 48.91 |
| 14 | 65.22 | 37.18 | 34.14 | 39.33 | 49.04 |
| 15 | 65.13 | 36.56 | 34.35 | 39.34 | 49.16 |
| 16 | 65.08 | 35.93 | 34.61 | 39.33 | 49.28 |
| 17 | 65.04 | 35.42 | 34.9 | 39.33 | 49.35 |
| 18 | 64.96 | 34.93 | 35.15 | 39.42 | 49.43 |
| 19 | 64.9 | 34.47 | 35.36 | 39.44 | 49.77 |
| 20 | 64.84 | 34.17 | 35.53 | 39.47 | 50.01 |

Example 3

Mouthwash Formulation

A mouthwash containing TBZC-lys/Cysteine as active ingredient is formulated with the ingredients shown in Table 1.

TABLE I

| Ingredients | % | Loading (g) |
|---|---|---|
| Sorbitol 70% sol | 5.5% | 27.5 |
| Aqueous TBZC solution 2.53% Zn plus 0.5% cysteine | 40% | 200 |
| Na Saccharin | 0.02% | 0.1 |
| Propylene Glycol | 7% | 35 |
| Poloxomer 407 | 0.4% | 9 |
| Citric Acid | 0.02% | 0.1 |
| Potassium Sorbitol | 0.05% | 0.25 |
| Glycerin | 7.5% | 37.5 |
| Flavor | 0.1% | 0.5 |
| Deionized water | Q.S. | Q.S. |
| Total | 100% | 500 |
| Zn % | 1% | |

The formulation can form a clear, stable solution but generates a precipitate when diluted. This mouthwash formulation has a neutral pH and is stable at 37° C. and on the shelf, but precipitates at dilute solution. This formation of insoluble precipitate by dilution allows formation of "plugs" in dentine tubules, providing benefits for hypersensitivity.

Example 4

Gel Formulations Comprising TBZC-Lysine

The mouthwash formulation of the preceding example provides a clear formulation and precipitation when diluted by water. This unique property facilitates anti-sensitive and anti-cavity effects, and it is thus of interest in a toothpaste product.

A gel with TBZC-Lys/cysteine as active ingredient is formulated with the ingredients shown in Table II. The clarity and the precipitation by dilution is evaluated. Zinc ion concentration in the following batches is at 0.5% (w/w) zinc level.

TABLE II

Oral gel with TBZC-Lys/cysteine

| Ingredients | % | Loading (g) |
|---|---|---|
| Sorbitol 70% sol | 76% | 380.15 |
| Aqueous TBZC-Lys solution 2.53% Zn plus 0.5% cysteine | 20% | 100 |
| Carboxymethyl cellulose (CMC) and Trimethyl cellulose (TMC) | 0.7% | 3.5 |
| Na Saccharin | 0.27% | 1.35 |
| Propylene Glycol | 3% | 15 |
| Total | 100% | 500 |
| % Zn | 0.506% | 2.53 |

The gel can be used alone or in a toothpaste having a gel phase and an abrasive paste phase. TBZC-Lys/cysteine as active ingredient in gel phase of toothpaste formulation. The formation of insoluble precipitate by dilution facilitates the formation of "plugs" in dentine tubules after using this type of toothpaste, and moreover, it provides a white precipitate signal during consumer use.

Example 6

Dentifrice Formulation Comprising TBZC-Lys/Cysteine

Test dentifrice comprising ZLC/cysteine, 1450 ppm fluoride, and phosphates is prepared as follows:

TABLE III

| Ingredient | Weight % |
| --- | --- |
| PEG600 | 3 |
| CMC-7 | 0.65 |
| Xanthan | 0.2 |
| Sorbitol | 27 |
| Glycerin | 20 |
| Saccharin | 0.3 |
| Calcium pyrophosphate | 0.25 |
| Sodium phosphate dibasic | 3.5 |
| Sodium fluoride (to provide 1450 ppm fluoride) | 0.32 |
| Water | QS |
| Titanium dioxide | 0.5 |
| Abrasive silica | 8 |
| Thickener silica | 8 |
| Aqueous TBZC-Lys solution 2.53% Zn plus 0.5% cysteine | 20 |
| Sodium lauryl sulfate | 1.5 |
| Flavoring | 1.2 |

The invention claimed is:

1. A composition comprising (i) a tetrabasic zinc-amino acid halide complex and (ii) cysteine in free or in orally or cosmetically acceptable salt form; wherein the amino acid is lysine, and wherein the composition comprises an amount of cysteine effective to provide a precipitate after a four-fold or higher dilution with water.

2. The composition according to claim 1, wherein the tetrabasic zinc-amino acid complex is formed from precursors, wherein the precursors are tetrabasic zinc chloride, an amino acid source, and a chloride source, wherein part of the chloride source can be the amino acid source, or hydrochloric acid.

3. The composition according to claim 1, wherein the tetrabasic zinc halide is tetrabasic zinc chloride.

4. The composition according to claim 1, wherein the tetrabasic zinc halide amino acid complex is made by combining tetrabasic zinc chloride with an amino acid hydrochloride or a free basic amino acid.

5. The composition according to claim 1, which upon dilution with water, provides a precipitate comprising an insoluble zinc-containing complex.

6. The composition according to claim 1, which instantly forms a precipitate upon a four-fold or higher dilution with water.

7. The composition according to claim 1, comprising an amount of cysteine effective to provide delayed precipitation after a four-fold or higher dilution with water.

8. The composition according to claim 1, capable of forming a precipitate upon a four-fold or higher dilution with water, wherein the precipitate is resistant to acid at least at a pH of 5.5.

9. The composition according to claim 1, wherein the total amount of zinc present in the composition is 0.2 to 8% by weight of the composition.

10. The composition according to claim 1, having a pH of 8.4 to 8.8 before dilution.

11. The composition of claim 1, wherein the amount of cysteine is 0.05 to 0.5% by weight.

12. The composition of claim 1, wherein the cysteine is a cysteine hydrohalide.

13. The composition according to claim 1, which is an antiperspirant or deodorant product, further comprising a cosmetically acceptable carrier.

14. The composition of claim 1 which is a personal care product selected from liquid hand soap, body wash, dermal lotions, dermal creams, and dermal conditioners further comprising a cosmetically acceptable carrier.

15. The composition of claim 1 which is an oral care product, further comprising an orally acceptable carrier.

16. A method of killing bacteria, reducing perspiration, and/or reducing body odor comprising applying to skin an effective amount of the composition of claim 14.

17. A method of killing bacteria, treating or reducing the incidence of acne or topical skin infections, or to provide a visual signal when washing comprising washing the skin with water and an effective amount of the composition of claim 14.

18. A method to reduce and inhibit acid erosion of the enamel, clean the teeth, reduce bacterially-generated biofilm and plaque, reduce gingivitis, inhibit tooth decay and formation of cavities, and/or reduce dentinal hypersensitivity comprising applying an effective amount of a composition according to claim 15 to the oral cavity of a person in need thereof.

* * * * *